(12) United States Patent
Chang et al.

(10) Patent No.: US 9,797,892 B2
(45) Date of Patent: *Oct. 24, 2017

(54) MOLECULAR BIOSENSORS CAPABLE OF SIGNAL AMPLIFICATION

(71) Applicants: Saint Louis University, St. Louis, MO (US); Mediomics LLC, St. Louis, MO (US)

(72) Inventors: Yie-Hwa Chang, St. Louis, MO (US); Ling Tian, St. Louis, MO (US); Tomasz Heyduk, Ballwin, MO (US)

(73) Assignees: SAINT LOUIS UNIVERSITY, St. Louis, MO (US); MEDIOMICS LLC, St. Louis, MO (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/719,867

(22) Filed: May 22, 2015

(65) Prior Publication Data

US 2015/0253315 A1  Sep. 10, 2015

Related U.S. Application Data

(63) Continuation of application No. 13/578,718, filed as application No. PCT/US2011/024547 on Feb. 11, 2011, now Pat. No. 9,040,287.

(60) Provisional application No. 61/303,914, filed on Feb. 12, 2010.

(51) Int. Cl.
| | |
|---|---|
| *C12M 1/34* | (2006.01) |
| *C12Q 1/68* | (2006.01) |
| *C07H 21/04* | (2006.01) |
| *G01N 31/22* | (2006.01) |

(Continued)

(52) U.S. Cl.
CPC ......... *G01N 33/542* (2013.01); *C12Q 1/6804* (2013.01); *C12Q 1/6818* (2013.01); *C12Q 1/6823* (2013.01); *G01N 33/54326* (2013.01); *G01N 33/54353* (2013.01)

(58) Field of Classification Search
CPC .......... C12Q 1/68; C12Q 1/683; C07H 21/02; C12N 15/66; C12M 1/34
USPC .............. 435/6.1, 7.2, 183, 287.2; 536/24.3; 422/430

See application file for complete search history.

(56) References Cited

U.S. PATENT DOCUMENTS

| | | | |
|---|---|---|---|
| 4,894,347 A | 1/1990 | Hillyard et al. | |
| 5,270,163 A | 12/1993 | Gold et al. | |
| 5,475,096 A | 12/1995 | Gold et al. | |

(Continued)

FOREIGN PATENT DOCUMENTS

| | | |
|---|---|---|
| JP | 2003-508729 A | 3/2003 |
| WO | 97/00446 A1 | 1/1997 |

(Continued)

OTHER PUBLICATIONS

Abravaya et al., "Detection of point mutations with a modified ligase chain reaction (Gap-LCR)," Nucleic Acids Research, 1995, pp. 675-682, vol. 23, No. 4.

(Continued)

*Primary Examiner* — Narayan Bhat
(74) *Attorney, Agent, or Firm* — Polsinelli PC

(57) ABSTRACT

The present invention provides molecular biosensors capable of signal amplification, and methods of using the molecular biosensors to detect the presence of a target molecule.

10 Claims, 16 Drawing Sheets
(10 of 16 Drawing Sheet(s) Filed in Color)

(51) Int. Cl.
  *G01N 33/542* (2006.01)
  *G01N 33/543* (2006.01)

(56) References Cited

U.S. PATENT DOCUMENTS

| | | | |
|---|---|---|---|
| 5,476,766 A | 12/1995 | Gold et al. |
| 5,543,293 A | 8/1996 | Gold et al. |
| 5,567,588 A | 10/1996 | Gold et al. |
| 5,582,981 A | 12/1996 | Toole et al. |
| 5,637,459 A | 6/1997 | Burke et al. |
| 5,641,629 A | 6/1997 | Pitner et al. |
| 5,650,275 A | 7/1997 | Pitner et al. |
| 5,660,985 A | 8/1997 | Pieken et al. |
| 5,670,637 A | 9/1997 | Gold et al. |
| 5,683,867 A | 11/1997 | Biesecker et al. |
| 5,688,935 A | 11/1997 | Stephens et al. |
| 5,696,249 A | 12/1997 | Gold et al. |
| 5,705,337 A | 1/1998 | Gold et al. |
| 5,712,375 A | 1/1998 | Jensen et al. |
| 5,723,289 A | 3/1998 | Eaton et al. |
| 5,723,592 A | 3/1998 | Eaton et al. |
| 5,750,342 A | 5/1998 | Stephens et al. |
| 5,756,291 A | 5/1998 | Griffin et al. |
| 5,763,566 A | 6/1998 | Jensen et al. |
| 5,763,595 A | 6/1998 | Gold et al. |
| 5,773,598 A | 6/1998 | Burke et al. |
| 5,789,157 A | 8/1998 | Jensen et al. |
| 5,789,160 A | 8/1998 | Eaton et al. |
| 5,817,785 A | 10/1998 | Gold et al. |
| 5,840,867 A | 11/1998 | Toole et al. |
| 5,843,653 A | 12/1998 | Gold et al. |
| 5,853,984 A | 12/1998 | Davis et al. |
| 5,858,660 A | 1/1999 | Eaton et al. |
| 5,861,254 A | 1/1999 | Schneider et al. |
| 5,864,026 A | 1/1999 | Jensen et al. |
| 5,874,218 A | 2/1999 | Drolet et al. |
| 5,958,691 A | 9/1999 | Pieken et al. |
| 5,962,219 A | 10/1999 | Gold et al. |
| 5,989,823 A | 11/1999 | Jayasena et al. |
| 5,998,142 A | 12/1999 | Gold et al. |
| 6,001,570 A | 12/1999 | Grossman |
| 6,001,577 A | 12/1999 | Gold et al. |
| 6,011,020 A | 1/2000 | Gold et al. |
| 6,013,443 A | 1/2000 | Heilig et al. |
| 6,024,918 A | 2/2000 | Hendriks |
| 6,030,776 A | 2/2000 | Eaton et al. |
| 6,048,698 A | 4/2000 | Eaton et al. |
| 6,083,696 A | 7/2000 | Biesecker et al. |
| 6,110,900 A | 8/2000 | Gold et al. |
| 6,114,120 A | 9/2000 | Jensen et al. |
| 6,127,119 A | 10/2000 | Stephens et al. |
| 6,147,204 A | 11/2000 | Gold et al. |
| 6,177,555 B1 | 1/2001 | Jayasena et al. |
| 6,207,388 B1 | 3/2001 | Grossman |
| 6,225,058 B1 | 5/2001 | Munishkin et al. |
| 6,261,774 B1 | 7/2001 | Pagratis et al. |
| 6,261,783 B1 | 7/2001 | Jayasena et al. |
| 6,287,772 B1 | 9/2001 | Stefano et al. |
| 6,291,184 B1 | 9/2001 | Gold et al. |
| 6,300,074 B1 | 10/2001 | Gold et al. |
| 6,329,145 B1 | 12/2001 | Janjic et al. |
| 6,331,398 B1 | 12/2001 | Gold et al. |
| 6,344,318 B1 | 2/2002 | Gold et al. |
| 6,376,190 B1 | 4/2002 | Gold et al. |
| 6,380,377 B1 | 4/2002 | Dattagupta |
| 6,391,593 B1 | 5/2002 | Weston et al. |
| 6,399,302 B1 | 6/2002 | Lannigan et al. |
| 6,423,493 B1 | 7/2002 | Gorenstein et al. |
| 6,451,588 B1 | 9/2002 | Egholm et al. |
| 6,465,188 B1 | 10/2002 | Gold et al. |
| 6,506,887 B1 | 1/2003 | Smith et al. |
| 6,511,809 B2 | 1/2003 | Baez et al. |
| 6,544,746 B2 | 4/2003 | Heyduk |
| 6,566,495 B1 | 5/2003 | Fodor et al. |
| 6,593,091 B2 | 7/2003 | Keys et al. |
| 6,613,526 B2 | 9/2003 | Heilig et al. |
| 6,680,377 B1 | 1/2004 | Stanton et al. |
| 6,716,583 B2 | 4/2004 | Gold et al. |
| 6,730,482 B2 | 5/2004 | Gold et al. |
| 6,815,164 B2 | 11/2004 | Kurn |
| 6,878,515 B1 | 4/2005 | Landegren |
| 6,916,613 B2 | 7/2005 | Munishkin et al. |
| 7,125,660 B2 | 10/2006 | Stanton et al. |
| 7,172,865 B2 | 2/2007 | Heyduk |
| 7,282,328 B2 | 10/2007 | Kong et al. |
| 7,306,904 B2 | 12/2007 | Landegren et al. |
| 7,419,835 B2 | 9/2008 | Torres et al. |
| 7,435,542 B2 | 10/2008 | Shi et al. |
| 7,576,192 B2 | 8/2009 | Heyduk |
| 7,795,009 B2 | 9/2010 | Heyduk |
| 7,811,809 B2 | 10/2010 | Heyduk et al. |
| 7,939,313 B2 | 5/2011 | Heyduk et al. |
| 8,431,388 B2 | 4/2013 | Heyduk |
| 8,592,202 B2 | 11/2013 | Heyduk |
| 8,945,840 B2 | 2/2015 | Heyduk |
| 8,956,857 B2 | 2/2015 | Heyduk |
| 8,993,245 B2 | 3/2015 | Heyduk |
| 9,040,287 B2 | 5/2015 | Chang |
| 9,618,505 B2 | 4/2017 | Heyduk |
| 9,671,403 B2 | 6/2017 | Heyduk |
| 2002/0022224 A1 | 2/2002 | Hornby et al. |
| 2002/0037506 A1 | 3/2002 | Lin et al. |
| 2002/0051986 A1 | 5/2002 | Baez et al. |
| 2002/0064779 A1 | 5/2002 | Landegren et al. |
| 2003/0087239 A1 | 5/2003 | Stanton et al. |
| 2003/0207271 A1 | 11/2003 | Holwitt et al. |
| 2003/0224435 A1 | 12/2003 | Seiwert et al. |
| 2003/0232383 A1 | 12/2003 | Daunert et al. |
| 2003/0232388 A1 | 12/2003 | Kreimer et al. |
| 2004/0053310 A1 | 3/2004 | Shi et al. |
| 2004/0058378 A1 | 3/2004 | Kong et al. |
| 2004/0067501 A1 | 4/2004 | Kage |
| 2004/0180360 A1 | 9/2004 | Wilson et al. |
| 2004/0219523 A1 | 11/2004 | Stanton et al. |
| 2005/0009050 A1 | 1/2005 | Nadeau et al. |
| 2005/0069910 A1 | 3/2005 | Turner et al. |
| 2005/0089890 A1 | 4/2005 | Cubicciotti |
| 2005/0089899 A1 | 4/2005 | Cubicciotti |
| 2005/0095627 A1 | 5/2005 | Kolman et al. |
| 2005/0106594 A1 | 5/2005 | Ellington et al. |
| 2005/0112710 A1 | 5/2005 | Torres et al. |
| 2005/0221408 A1 | 10/2005 | Nalefski et al. |
| 2006/0110739 A1 | 5/2006 | Heyduk et al. |
| 2007/0154899 A1 | 7/2007 | Coull et al. |
| 2007/0287197 A1 | 12/2007 | Harris et al. |
| 2008/0044826 A1 | 2/2008 | Heyduk |
| 2008/0044834 A1 | 2/2008 | Heyduk |
| 2008/0171322 A1 | 7/2008 | Heyduk et al. |
| 2009/0202990 A1 | 8/2009 | Heyduk et al. |
| 2010/0021899 A1 | 1/2010 | Ikebukuro et al. |
| 2010/0041049 A1* | 2/2010 | Smith ............... C12Q 1/682 435/6.12 |
| 2010/0297654 A1 | 11/2010 | Heyduk |
| 2011/0091893 A1 | 4/2011 | Heyduk et al. |
| 2012/0028242 A1 | 2/2012 | Heyduk et al. |
| 2013/0034846 A1 | 2/2013 | Chang et al. |
| 2014/0243208 A1 | 8/2014 | Chang et al. |
| 2014/0248710 A1 | 9/2014 | Heyduk et al. |
| 2015/0191779 A1 | 7/2015 | Heyduk |
| 2015/0219668 A1 | 8/2015 | Heyduk |
| 2015/0253315 A1 | 9/2015 | Chang |
| 2016/0077088 A1 | 3/2016 | Chang |

FOREIGN PATENT DOCUMENTS

| | | |
|---|---|---|
| WO | 00/70329 A1 | 11/2000 |
| WO | 03/064657 A1 | 8/2003 |
| WO | 03/078449 A2 | 9/2003 |
| WO | 2005/059509 A2 | 6/2005 |
| WO | 2006/128138 A1 | 11/2006 |
| WO | 2006/135527 A2 | 12/2006 |
| WO | 2007/005649 A2 | 1/2007 |
| WO | 2008/108873 A2 | 9/2008 |
| WO | 2010/059820 A1 | 5/2010 |

(56) References Cited

FOREIGN PATENT DOCUMENTS

| WO | 2011/100561 A1 | 8/2011 |
|---|---|---|
| WO | 2013/016280 A2 | 1/2013 |
| WO | 2016/040830 A1 | 3/2016 |

OTHER PUBLICATIONS

Bevan et al., "Sequencing of PCR-amplified DNA," PCR Methods and Applications, 1992, pp. 222-228, vol. 1.
Bock et al., "Selection of single-stranded DNA molecules that bind and inhibit human thrombin," Nature, 1992, pp. 564-566, vol. 355.
Boder et al., "Yeast surface display for screening combinatorial polypeptide libraries," Nat. Biotech., 1997, pp. 553-557, vol. 15, No. 6.
Burgstaller et al., "Synthetic Ribozymes and the First Deoxyribozyme," Angew. Chem. Int. Ed. Engl., 1995, pp. 1189-1192, vol. 34, No. 11.
"Chemical bond," http://en.wikipedia.org/wiki/Chemicalbond, printed Jun. 24, 2008; 11 pgs.
Daniels et al., "Generation of RNA Aptamers to the G-Protein-Coupled Receptor for Neurotensin, NTS-1," Analytical Biochemistry, 2002, pp. 214-226, vol. 305.
Decision of Refusal from related Japanese Patent Application No. 2006-543991, dated Aug. 23, 2011; 3 pgs. (with English translation).
Decision on Oral Proceedings from related European Patent Application No. 04813618.8, dated May 26, 2010; 7 pgs.
Decision to Grant from related European Patent Application No. 07873908.3, dated Sep. 5, 2013; 2 pgs.
Decision to Grant from related European Patent Application No. 06770407.2, dated Nov. 14, 2011; 5 pgs.
Ellington et al., "In vitro selection of RNA molecules that bind specific ligands," Nature, 1990, pp. 818-822, vol. 346.
Extended European Search Report from related European Patent Application No. 07873908.3, dated Dec. 22, 2009; 6 pgs.
European Supplementary Search Report from related European Patent Application No. 04813618.8, dated Apr. 23, 2008; 2 pgs.
Extended European Search Report from related European Patent Application No. 06770407.2, dated Jul. 9, 2010; 4 pgs.
Extended European Search Report from related European Patent Application No. 13194822.6, dated Jan. 17, 2014; 6 pgs.
Extended European Search Report from related European Patent Application No. 11742872.2, dated Aug. 23, 2013; 6 pgs.
Famulok et al., "In Vitro Selection of Specific Ligand binding Nucleic Acids," Angew. Chem. Int. Ed. Engl., 1992, pp. 979-988, vol. 31.
Famulok et al., "Selection of Functional RNA and DNA Molecules from Randomized Sequences," Nucl. Acids and Mol. Biol., 1993, pp. 271-284, vol. 7.
Fang et al., "Synthetic DNA Aptamers to Detect Protein Molecular Variants in a High-Throughput Fluorescence Quenching Assay," Chem. Bio. Chem., 2003, pp. 829-834, vol. 4.
Francisco et al., "Production and fluorescence-activated cell sorting of Escherichia coli expressing a functional antibody fragment on the external surface," PNAS, 1993, pp. 10444-10448, vol. 90, No. 22.
Fredriksson et al., "Protein Detection Using Proximity-dependent DNA Ligation Assays," Nature Biotechnology, 2002, pp. 473-477, vol. 20.
Fried et al., "Equilibria and kinetics of lac repressor-operator interactions by polyacrylamide gel electrophoresis," Nucl. Acid Res., 1981, pp. 6505-6525, vol. 9, No. 23.
Georgiou et al., "Display of heterologous proteins on the surface of microorganisms: From the screening of combinatorial libraries to live recombinant vaccines," Nat. Biotech., 1997, pp. 29-34, vol. 15.
Gold et al., "Diversity of Oligonucleotide Functions," Ann. Rev. Biochem., 1995, pp. 763-797, vol. 64.
Hamaguchi et al., "Aptamer Beacons for the Direct Detection of Proteins," Analyt. Biochem., 2001, pp. 126-131, vol. 294.

Hanes et al., "In vitro selection and evolution of functional proteins by using ribosome display," PNAS, 1997, pp. 4937-4942, vol. 94.
Heyduk et al., "Nucleic Acid-Based Fluorescence Sensors for Detecting Proteins," Anal. Chem., 2005, pp. 1147-1156, vol. 77, No. 4.
Heyduk et al., "Conformational Changes of DNA Induced by Binding of Chironomus High Mobility Group Protein 1a (cHMG1a)," J. Biol. Chem., 1997, pp. 19763-19770, vol. 272, No. 32.
Heyduk et al., "Homogeneous Fluorescence Assay for Cyclic AMP," Comb. Chem. and High Throughput Screen., 2003, pp. 347-354, vol. 6, No. 4.
Heyduk et al., "Thiol-reactive, Luminescent Europium Chelates: Luminescence Probes for Resonance Energy Transfer Distance Measurements in Biomolecules," Anal. Biochem., 1997, pp. 216-227, vol. 248.
Heyduk et al., "Molecular beacons for detecting DNA binding proteins: mechanism of action," Analyt. Biochem., 2003, pp. 1-10, vol. 316.
Heyduk et al., "Luminescense Energy Transfer with Lanthanide Chelates: Interpretation of Sensitized Acceptor Decay Amplitudes," Analyt. Biochem., 2001, pp. 60-67, vol. 289, No. 1.
Heyduk et al., "Molecular beacons for detecting DNA binding proteins," Nat. Biotech., 2002, pp. 171-176, vol. 20.
Heyduk et al., "Molecular pincers: new antibody-based homogeneous protein sensors," Anal. Chem., 2008, pp. 5152-5159, vol. 80, No. 13.
Heyduk et al., "Fluorescent homogenous immunosensors for detecting pathogenic bacteria," Anal. Biochem., 2010, pp. 298-303, vol. 396, No. 2.
Hosse et al., "A new generation of protein display scaffolds for molecular recognition," Protein Science, 2006, pp. 14-27, vol. 15.
'HyTher—Hybridization Thermodynamics—Module 1', http://ozone3.chem.wayne.edu/cgi-bin/login/execs/HytherMI.cgi, printed Mar. 5, 2009; 1 page.
International Search Report and Written Opinion from related International Patent Application No. PCT/US2007/075560, dated Aug. 25, 2008; 10 pgs.
International Search Report and Written Opinion from related International Patent Application No. PCT/US2006/018845, dated Aug. 3, 2007; 8 pgs.
International Search Report and Written Opinion from related International Patent Application No. PCT/US2009/065142, dated Jan. 20, 2010; 7 pgs.
International Search Report and Written Opinion from related International Patent Application No. PCT/US2004/041315, dated Sep. 24, 2007; 6 pgs.
International Search Report and Written Opinion from related International Patent Application No. PCT/US12/47840, dated Jan. 11, 2013; 19 pgs.
Jayasena, "Aptamers: An Emerging Class of Molecules That Rival Antibodies in Diagnostics," Clin. J. Chem., 1999, pp. 1628-1650, vol. 45, No. 9.
Jeppesen et al., "Impact of Polymer Tether Length on Multiple Ligand-Receptor Bond Formation," Science, 2011, pp. 465-468, vol. 293.
Keefe et al., "Functional proteins from a random-sequence library," Nature, 2001, pp. 715-718, vol. 410, No. 6829.
Klug et al., "All you wanted to know about SELEX (but were afraid to ask . . . )," Mol. Biol. Reports, 1994, pp. 97-107, vol. 20.
Knoll et al., "Unimolecular Beacons for the Detection of DNA-Binding Proteins," Anal. Chem., 2004, pp. 1156-1164, vol. 76, No. 4.
Li et al., "Molecular Aptamer Beacons for Real-Time Protein Recognition," Biochem. and Biophys. Res. Commun., 2002, pp. 31-40, vol. 292, No. 1.
Lipovsek et al., "In-vitro protein evolution by ribosome display and mRNA display," J. Imm. Methods, 2004, pp. 51-67, vol. 290.
Mathis, "Probing Molecular Interactions with Homogeneous Techniques Based on Rare Earth Cryptrates and Fluorescence Energy Transfer," Clinic. Chem., 1995, pp. 1391-1397, vol. 41, No. 9.

(56) References Cited

OTHER PUBLICATIONS

Matlock et al., "Sequence Determinants for the Recognition of the Fork Junction DNA Containing the -10 Region of Promoter DNA by *E. coli* RNA Polymerase," Biochem., 2000, pp. 12274-12283, vol. 39, No. 40.
Mills et al., "Flexibility of Single-Stranded DNA: Use of Gapped Duplex Helices to Determine the Persistence Lengths of Poly(dT) and Poly(dA)," J. Mol. Biol., 1999, pp. 245-257, vol. 285.
Minutes of Oral Proceedings from related European Patent Application No. 04813618.8, dated May 20, 2010; 5 pgs.
Notice of Allowance from related Chinese Patent Application No. 200480036874.7, dated Feb. 29, 2012; 3 pgs. (English translation).
Notice of Allowance and Interview Summary from related U.S. Appl. No. 12/830,958, dated Dec. 20, 2012; 16 pgs.
Notice of Allowance from related U.S. Appl. No. 12/961,135, dated Jul. 24, 2013; 10 pgs.
Notice of Allowance from related U.S. Appl. No. 11/916,776, dated Aug. 5, 2014; 7 pgs.
Office Action from related European Patent Application No. 06770407.2, dated Apr. 4, 2011; 3 pgs.
Office Action from related European Patent Application No. 04813618.8, dated Dec. 18, 2008; 3 pgs.
Office Action from related European Patent Application No. 04813618.8, dated Jul. 1, 2008; 3 pgs.
Office Action from related European Patent Application No. 07873908.3, dated Jan. 4, 2012; 3 pgs.
Office Action from related European Patent Application No. 07873908.3, dated Oct. 26, 2010; 5 pgs.
Office Action from related Chinese Patent Application No. 200480036874.7, dated Aug. 9, 2010; 23 pgs. (with English translation).
Office Action from related Chinese Patent Application No. 200480036874.7, dated Jan. 19, 2011; 12 pgs. (with English translation).
Office Action from related Chinese Patent Application No. 200480036874.7, dated Jun. 23, 2011; 9 pgs. (with English translation).
Office Action from related Chinese Patent Application No. 200780037379.1, dated Oct. 10, 2011; 14 pgs. (with English translation).
Office Action from related Chinese Patent Application No. 200780037379.1, dated Jul. 10, 2012; 8 pgs. (with English translation).
Office Action from related Chinese Patent Application No. 200980146720.6, dated May 27, 2013; 18 pgs. (with English translation).
Office Action from related Chinese Patent Application No. 200980146720.6, dated Dec. 10, 2013; 34 pgs. (with English translation).
Office Action from related Chinese Patent Application No. 200980146720.6, dated May 20, 2014; 25 pgs. (with English translation).
Office Action from related Japanese Patent Application No. 2006-543991, dated Feb. 23, 2010; 6 pgs. (with English translation).
Office Action from related Japanese Patent Application No. 2006-543991, dated Nov. 24, 2010; 4 pgs. (with English translation).
Office Action from related Japanese Patent Application No. 2011-284014, dated Jul. 29, 2014; 1 page. (English translation only).
Office Action from related Japanese Patent Application No. 2011-284014, dated Oct. 8, 2013; 2 pgs. (English translation only).
Office Action from related Canadian Patent Application No. 2,545,006, dated Feb. 3, 2011; 5 pgs.
Office Action from related Canadian Patent Application No. 2,660,129, dated Aug. 21, 2013; 3 pgs.
Office Action from related Canadian Patent Application No. 2,787,483, dated Feb. 19, 2014; 3 pgs.
Office Action from related Canadian Patent Application No. 2,611,198, dated Nov. 20, 2012; 3 pgs.
Office Action from related Canadian Patent Application No. 2,611,198, dated Aug. 30, 2013; 2 pgs.
Office Action from related Canadian Patent Application No. 2,744,003, dated Dec. 27, 2013; 2 pgs.
Office Action from related Canadian Patent Application No. 2,744,003, dated Mar. 26, 2013; 3 pgs.
Office Action from related Indian Patent Application No. 1337/CHENP/2009, dated Nov. 27, 2013; 4 pgs. (English translation).
Office Action from related U.S. Appl. No. 12/961,135, dated Dec. 1, 2011; 23 pgs.
Office Action from related U.S. Appl. No. 12/961,135, dated Jun. 17, 2011; 17 pgs.
Office Action from related U.S. Appl. No. 10/539,107, dated Dec. 18, 2009; 22 pgs.
Office Action from related U.S. Appl. No. 10/539,107, dated Jul. 2, 2008; 21 pgs.
Office Action from related U.S. Appl. No. 10/539,107, dated Mar. 12, 2009; 23 pgs.
Office Action from related U.S. Appl. No. 11/916,776, dated Jun. 14, 2010; 9 pgs.
Office Action from related U.S. Appl. No. 11/916,776, dated Jun. 30, 2011; 12 pgs.
Office Action from related U.S. Appl. No. 11/836,339, dated Sep. 14, 2009; 16 pgs.
Office Action from related U.S. Appl. No. 11/836,339, dated Mar. 8, 2010; 14 pgs.
Office Action from related U.S. Appl. No. 11/836,333, dated Sep. 30, 2009; 32 pgs.
Office Action from related U.S. Appl. No. 12/830,958, dated May 8, 2012; 21 pgs.
Office Action from related U.S. Appl. No. 13/133,198, dated Nov. 5, 2012; 12 pgs.
Office Action from related U.S. Appl. No. 13/133,198, dated Jun. 27, 2013; 14 pgs.
Oligonucleotide Modifications (TriLink Products) screen from http://www.trilinkbiotech.com/products/oligo/details_modifications.asp?ProducUD=133, printed Sep. 8, 2009; 1 page.
Notice of Allowance from related Canadian Patent Application No. 2,611,198, dated Aug. 19, 2014; 1 page.
Heyduk, "Practical biophysics: Sensors for rapid detection of biological targets utilizing target-induced oligonucleotide annealing", Biophysical Chemistry, 2010, pp. 91-95, vol. 151.
Lass-Napiorkowska et al., "Detection Methodology Based on Target Molecule-Induced Sequence-Specific Binding to a Single-Stranded Oligonucleotide", Analytical Chemistry, 2012, pp. 3382-3389, vol. 84.
Notice of Allowance from related U.S. Appl. No. 13/133,198, dated Aug. 28, 2014; 13 pgs.
Notice of Allowance from related U.S. Appl. No. 13/728,226, dated Jun. 16, 2014; 21 pgs.
Office Action from related European Patent Application No. 13194822.6, dated Dec. 19, 2014; 4 pgs.
Office Action from related U.S. Appl. No. 13/728,226, dated Jan. 10, 2014; 30 pgs.
Order Rescheduling Oral Proceedings from related European Patent Application No. 04813618.8, dated Jan. 28, 2014; 1 page.
Ozawa et al., "Identification and Characterization of Peptides Binding to Newcastle Disease Virus by Phage Display," J. Vet. Med. Sci., 2005, pp. 1237-1241, vol. 67, No. 12.
Ratilainen et al., "Hybridization of Peptide Nucleic Acid," Biochemistry, 1998, pp. 12331-12342, vol. 37.
Request for Postponement of Oral Proceedings from related European Patent Application No. 04813618.8, dated Jan. 27, 2014; 1 page.
Response to Communication Under Article 15(1) of the Rules of Procedure of the Board of Appeals from related European Patent Application No. 04813618.8, dated Aug. 1, 2014; 8 pgs.
Result of Telephone Consultation with Examiner from related European Patent Application No. 04813618.8, dated Apr. 13, 2010; 3 pgs.
Roberts et al., "RNA-peptide fusions for the in vitro selection of peptides and proteins," PNAS, 1997, pp. 12297-12302, vol. 94, No. 23.
Rockett et al., "DNA arrays: technology, options and toxicological applications," Xenobiotica, 2000, pp. 155-177, vol. 30, No. 2.

(56) References Cited

OTHER PUBLICATIONS

Santalucia et al., "Improved Nearest-Neighbor Parameters for Predicting DNA Duplex Stability," Biochemistry, 1996, pp. 3555-3562, vol. 35, No. 11.
Santalucia, "A unified view of polymer, dumbbell, and oligonucleotide DNA nearest-neighbor thermodynamics," PNAS, 1998, pp. 1460-1465, vol. 95.
Sayer et al., "Structural characterization of a 2'F-RNA aptamer that binds a HIV-1 SU glycoprotein, g120," Biochem. and Biophysic. Res. Comm., 2002, pp. 924-931, vol. 293.
Selvin et al., "Luminescence energy transfer using a terbium chelate: Improvements on fluorescence energy transfer," Proc. Natl. Acad. Sci. USA, 1994, pp. 10024-10028, vol. 91.
Selvin et al., "Luminescence Resonance Energy Transfer," J. Am. Chem. Soc., 1994, pp. 6029-6030, vol. 116.
Sen et al., "On the stability of peptide nucleic acid duplexes in the presence of organic solvents," Nucleic Acids Research, 2007, pp. 3367-3374, vol. 35, No. 10.
Sequence alignment brochure SEQ ID No. 1 and 2, http://blast.ncbi.nlm.nih.gov/Blast.cgi, printed Sep. 13, 2009; 4 pgs.
Sequence alignment brochure SEQ ID No. 1 and 3, http://blast.ncbi.nlm.nih.gov/Blast.cgi, printed Sep. 15, 2009; 4 pgs.
Sequence alignment brochure SEQ ID No. 2 and 3, http://blast.ncbi.nlm.nih.gov/Blast.cgi, printed Sep. 13, 2009; 4 pgs.
Sequence alignment brochure SEQ ID No. 5 and 12, http://blast.ncbi.nlm.nih.gov/Blast.cgi, printed Sep. 13, 2009; 4 pgs.
Sequence alignment brochure SEQ ID No. 7 and 12, http://blast.ncbi.nlm.nih.gov/Blast.cgi, printed Sep. 15, 2009; 4 pgs.
Statement of Grounds for Appeal from related European Patent Application No. 04813618.8, dated Oct. 15, 2010; 22 pgs.
Stoltenburg et al., "SELEX—A (r)evolutionary method to generate high-affinity nucleic acid ligands", Biomolecular Engineering, 2007, pp. 381-403, vol. 24.
Summons to Oral Proceedings from related European Patent Application No. 04813618.8, dated Dec. 19, 2013; 1 page.
Supplementary European Search Report from related European Patent Application No. 12817830.8, dated Nov. 25, 2014; 11 pgs.
Tanaka et al., "Specificity of Hybridization Between DNA Sequences Based on Free Energy," DNA Computing, 2006, pp. 371-379, Springer-Verlag Berlin Heidelberg.
Tasset et al., "Oligonucleotide Inhibitors of Human Thrombin that Bind Distinct Epitopes," J. Mol. Biol., 1997, pp. 688-698, vol. 272, No. 5.
Telephone Consultation Records faxed May 6, 2010 regarding telephone interviews held on Apr. 27 and May 3, 2010 from related European Patent Application No. 04813618.8; 5 pgs.
Tuerk et al., "Systematic Evolution of Ligands by Exponential Enrichment: RNA Ligands to Bacteriophage T4 DNA Polymerase," Science, 1990, pp. 505-510, vol. 249, No. 4968.
Uptima FT-UP17412 SMCC sSMCC Heterobifunctional cross-linkers brochure, undated (no date was provided); 3 pgs., in Office Action dated Jul. 2, 2008 from related U.S. Appl. No. 10/539,107.
Uptima FT-UP79042 SPDP, Ic-SPDP, Sulfo-Ic-SPDP Heterobifunctional cross-linkers brochure, undated (date provided was Sep. 15, 2009); 3 pgs., Office action dated Sep. 30, 2009 from related U.S. Appl. No. 11/836,333.
Wilson et al., "In Vitro Selection of Functional Nucleic Acids," Ann. Rev. Biochem., 1999, pp. 611-647, vol. 68.
Written Submissions from related European Patent Application No. 04813618.8, dated Apr. 30, 2010; 37 pgs.
Written Submissions from related European Patent Application No. 04813618.8, dated Apr. 22, 2010; 15 pgs.
Written Submissions from related European Patent Application No. 04813618.8, dated Apr. 6, 2010; 16 pgs.
Xu et al., "Anti-peptide aptamers recognize amino acid sequence and bind a protein epitope," Proc. Natl. Acad. Sci. USA, 1996, pp. 7475-7480, vol. 93.
Yamamoto et al., "Molecular beacon aptamer fluoresces in the presence of Tat protein of HIV-1," Genes to Cells, 2000, pp. 389-396, vol. 5.

Zalipsky, "Chemistry of polyethylene glycol conjugates with biologically active molecules," Advanced Drug Delivery Reviews, 1995, pp. 157-182, vol. 16.
Zhang et al., "A Simple Statistical Parameter for Use in Evaluation and Validation of High Throughput Screening Assays," J. Biomol. Screening, 1999, pp. 67-73, vol. 4, No. 2.
Darmanis et al, "Self-assembly of proximity probes for flexible and modular proximity ligation assays", BioTechniques, 2007, pp. 443-450, vol. 43, No. 4.
International Search Report and Written Opinion from related International Patent Application No. PCT/ US2015/049733, dated Jan. 29, 2016; 15 pages.
Office Action from related U.S. Appl. No. 14/234,329, dated Apr. 1, 2016; 10 pages.
Office Action from related U.S. Appl. No. 14/623,348, dated Jun. 17, 2016; 21 pages.
International Search Report and Written Opinion dated Jun. 28, 2011 from related International Patent Application No. PCT/US2011/024547, 10 pages.
Notice of Allowance and Fee (s) Due related to Application No. 11/916,776 dated Sep. 19, 2014 with 5 pages.
Notice of Allowance dated Oct. 1, 2014 from related U.S. Appl. No. 13/728,226; 8 pages.
Notice of Allowance dated Nov. 18, 2014 from related U.S. Patent Appl. No. 13/133,198; 8 pages.
Notice of Allowance dated Jan. 27, 2015 from related U.S. Appl. No. 13/578,718; 11 pages.
Notice of Allowance dated Feb. 10, 2015 from related Canadian Patent Application No. 2,660,129; 1 page.
Office Action dated Jan. 8, 2015 from related European Patent Application No. 03703998.9, 2 pages.
Office Action dated May 30, 2012 from related European Patent Application No. 03703998.9, 3 pages.
Office Action from related Chinese Patent Application No. 201280038577.0, dated Jul. 7, 2015; 15 pages.
Office Action dated Nov. 3, 2014 from related Chinese Patent Application No. 201280038577.0; 11 pages.
Office Action dated Mar. 9, 2015 from related Canadian Patent Application No. 2,787,483; 4 pages.
Office Action dated Oct. 1, 2008 from related U.S. Appl. No. 11/609,628; 13 pages.
Office Action dated May 19, 2014 from related European Patent Application No. 117428722; 3 pages.
Office Action dated Apr. 2, 2015 from related European Patent Application No. 11742872.2; 4 pages.
Office Action from related U.S. Appl. No. 14/234,329, dated Aug. 7, 2015; 44 pages.
Final Office Action dated Nov. 5, 2014 from related U.S. Patent Application No. 13/578,718; 25 pages.
Office Action dated Jan. 19, 2011 from related Chinese Patent Application No. 200480036874.7, with 7 pages of English translation.
Office Action dated Nov. 24, 2010 from related Japanese Patent Application No. 2006-543991, 2 pages with English translation.
Office Action dated Sep. 8, 2011 from related Chinese Patent Application No. 200480036874.7, 5 pages with English translation.
Office Action dated Sep. 13, 2013 from related U.S. Appl. No. 13/578,718, 24 pages.
Office Action with Interview Summary dated Feb. 21, 2014 from related U.S. Appl. No. 13/578,718, 32 pages.
Response to Communication Under Article 15(1) of the Rules of Procedure of the Board of Appeals dated Aug. 1, 2014 from related European Patent Application No. 04813618.8, 8 pages.
Supplementary European Search Report dated Jun. 11, 2010 from elated EP Application No. Ep 06770407, 1 page.
European Search Report dated Nov. 16, 2009, from related Application No. EP 07873908, 2 pages.
Final Office Action dated Aug. 3, 2010 from related U.S. Appl. No. 11/836,339, 13 pages.
Office Action dated May 30, 2016 from related Canadian Patent Application No. 2,787,483; 3 pages.
Office Action from related U.S. Appl. No. 14/234,329, dated Nov. 16, 2016; 13 pages.

(56) References Cited

OTHER PUBLICATIONS

Notice of Allowance dated Nov. 25, 2016 from related U.S. Appl. No. 14/623,348; 14 pages.
Office Action from related U.S. Appl. No. 14/673,336, dated Aug. 8, 2016; 60 pages.
Notice of Allowance dated Jan. 31, 2017 from related U.S. Appl. No. 14/673,336; 10 pages.
Office Action from related U.S. Appl. No. 14/719,867, dated Nov. 8, 2016; 68 pages.
Notice of Allowance dated Apr. 24, 2017 from related U.S. Appl. No. 141/719,867; 10 pages.

* cited by examiner

MOLECULAR BIOSENSORS CAPABLE OF SIGNAL AMPLIFICATION

CROSS REFERENCE TO RELATED APPLICATIONS

This application is a continuation of U.S. application Ser. No. 13/578,718, filed Sep. 14, 2012 which is a US National application of PCT Application PCT/US2011/024547, filed Feb. 11, 2011, which claims the priority of U.S. provisional application No. 61/303,914, filed Feb. 12, 2010, each of which is hereby incorporated by reference in its entirety.

FIELD OF THE INVENTION

The invention relates to molecular biosensors capable of signal amplification. The biosensors may be used to determine whether a target molecule is present in a sample.

BACKGROUND OF THE INVENTION

The detection, identification and quantification of specific molecules in our environment, food supply, water supply and biological samples (blood, cerebral spinal fluid, urine, et cetera) can be very complex, expensive and time consuming. Methods utilized for detection of these molecules include gas chromatography, mass spectroscopy, DNA sequencing, immunoassays, cell-based assays, biomolecular blots and gels, and myriad other multi-step chemical and physical assays.

There continues to be a high demand for convenient methodologies for detecting and measuring the levels of specific proteins in biological and environmental samples. Detecting and measuring levels of proteins is one of the most fundamental and most often performed methodologies in biomedical research. While antibody-based protein detection methodologies are enormously useful in research and medical diagnostics, they are typically not well adapted to rapid, high throughput parallel protein detection. Hence, there is a need in the art for effective, simple signal amplification and detection means.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
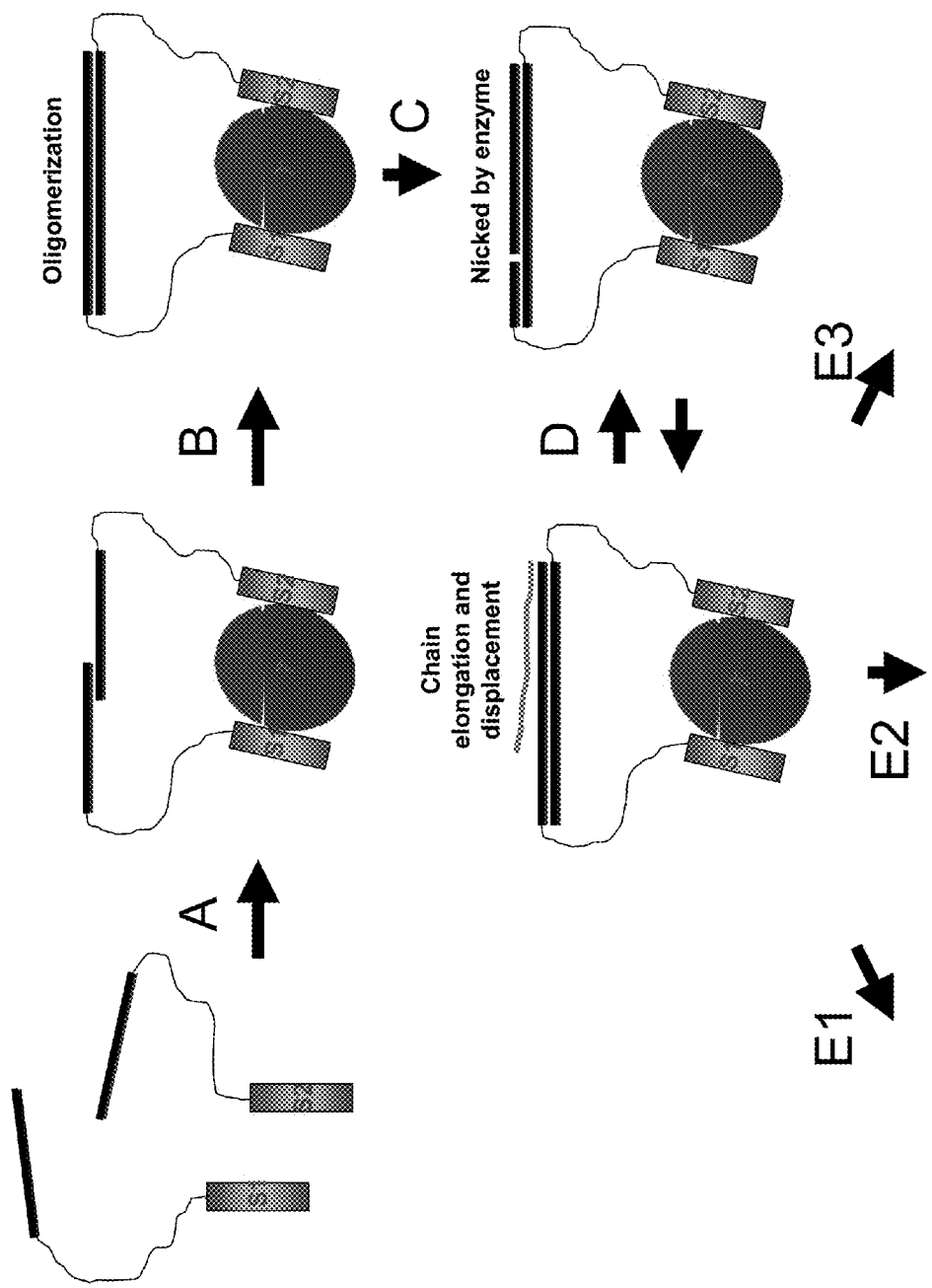
FIG. 1 depicts the overall design and function of a two-component molecular biosensor comprising a single nicking site.
Figure 1:
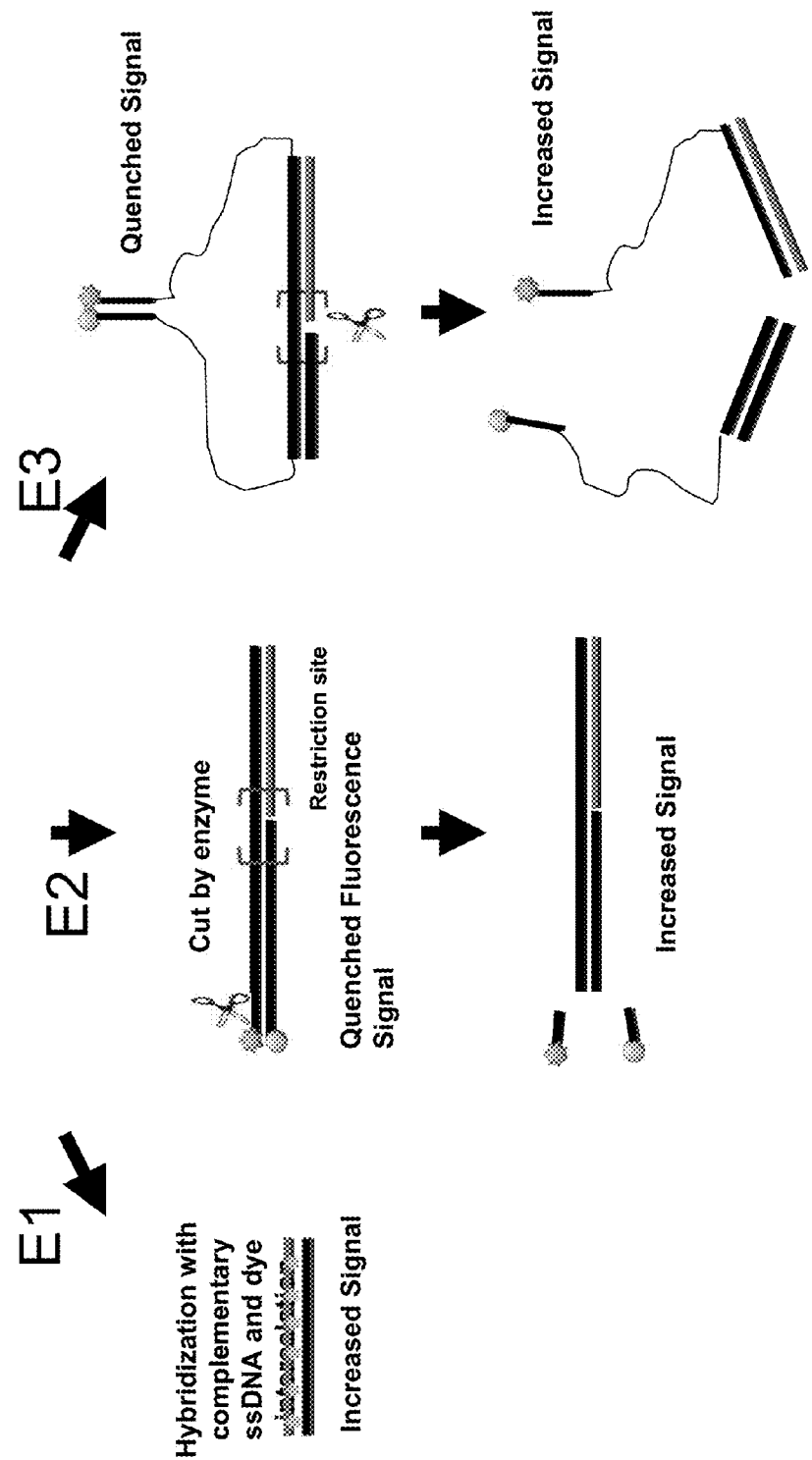

The present invention encompasses a molecular biosensor capable of signal amplification. Such a biosensor may be used to detect a target molecule. In one embodiment, the biosensor is comprised of two components, which comprise two epitope-binding agent constructs. Alternatively, in another embodiment, the biosensor is comprised of three components, which comprise two epitope-binding agent constructs and an oligonucleotide construct comprising a restriction enzyme recognition site. Each of these embodiments is discussed in more detail below.

Advantageously, a molecular biosensor of the invention, irrespective of the embodiment, is capable of signal amplification and provides a rapid homogeneous means to detect a variety of target molecules, including but not limited to proteins, carbohydrates, nucleic acids, macromolecules, and analytes.

I. Two-Component Molecular Biosensors

One aspect of the invention encompasses a two-component biosensor and methods of use thereof. For a two-component biosensor, detection of a target molecule typically involves target-molecule induced co-association of two epitope-binding agent constructs ($R^1$—$R^2$—$R^3$ and $R^4$—$R^5$—$R^6$) that each recognize distinct epitopes on the target molecule. The epitope-binding agent constructs each comprise a single-stranded nucleotide sequence ($R^3$ and $R^6$). Each single-stranded sequence comprises a complementary sequence ($R^8$ and $R^9$). Additionally, at least one single-stranded sequence comprises a restriction endonuclease recognition site ($R^7$). Association of the epitope binding agents ($R^1$ and $R^4$) with a target molecule results in annealing of the complementary sequences ($R^8$ and $R^9$) of the single-stranded nucleotide sequences, such that when the complementary regions are extended in the presence of a polymerase, a double-stranded endonuclease recognition site is reconstituted. The newly synthesized double-stranded recognition sequence may be nicked by a nicking restriction endonuclease that recognizes the reconstituted restriction enzyme recognition site. A DNA polymerase may then extend a second nucleic acid from the nick, thereby displacing the first nicked strand to form a displaced strand. The second extended strand may then be nicked, repeating the extension and displacement steps such that multiple copies of the displaced strand are produced, thereby amplifying the signal from the biosensor. The displaced strand may then be detected via several different methods.

The structure of the biosensor and methods of using the biosensor are discussed in more detail below.

(a) Biosensor Structure

In exemplary embodiments, a two-component molecular biosensor capable of signal amplification comprises two constructs, which together have formula (I):

$$R^1—R^2—R^3; \text{ and}$$

$$R^4—R^5—R^6; \quad (I)$$

wherein:
  $R^1$ is an epitope-binding agent that binds to a first epitope on a target molecule;
  $R^2$ is a flexible linker attaching $R^1$ to $R^3$;
  $R^3$ is a single stranded nucleotide sequence comprising $R^7$ and $R^8$;
    $R^7$ is a nucleotide sequence comprising at least one restriction endonuclease recognition site;
    $R^8$ is a nucleotide sequence complementary to $R^9$;
  $R^6$ is a single stranded nucleotide sequence comprising $R^9$;
    $R^9$ is a nucleotide sequence complementary to $R^8$, such that when $R^8$ and
    $R^9$ associate to form an annealed complex in the presence of a polymerase, $R^8$ and $R^9$ are extended by the polymerase to form a nucleotide sequence complementary to $R^7$, forming at least one double-stranded endonuclease recognition site;
  $R^5$ is a flexible linker attaching $R^4$ to $R^6$;
  $R^4$ is an epitope-binding agent that binds to a second epitope on a target molecule.

As will be appreciated by those of skill in the art, the choice of epitope binding agents, $R^1$ and $R^4$, in molecular biosensors having formula (I) can and will vary depending upon the particular target molecule. By way of example, when the target molecule is a protein, $R^1$ and $R^4$ may be an aptamer, or antibody. By way of further example, when $R^1$ and $R^4$ are double stranded nucleic acid the target molecule is typically a macromolecule that binds to DNA or a DNA binding protein. In general, suitable choices for $R^1$ and $R^4$ will include two agents that each recognize distinct epitopes on the same target molecule. In certain embodiments, however, it is also envisioned that $R^1$ and $R^4$ may recognize distinct epitopes on different target molecules. Non-limiting examples of suitable epitope binding agents may include agents selected from the group consisting of an aptamer, an antibody, an antibody fragment, a double-stranded DNA sequence, modified nucleic acids, nucleic acid mimics (e.g. LNA or PNA), a ligand, a ligand fragment, a receptor, a receptor fragment, a polypeptide, a peptide, a coenzyme, a coregulator, an allosteric molecule, a chemical entity and an ion.

In one embodiment, $R^1$ and $R^4$ are each aptamers having a sequence ranging in length from about 20 to about 110 bases. In another embodiment, $R^1$ and $R^4$ are each antibodies or antibody-like binders selected from the group consisting of polyclonal antibodies, ascites, Fab fragments, Fab' fragments, monoclonal antibodies, humanized antibodies, chimeric antibodies, single chain antibodies, and non-immunoglobulin scaffolds such as Affibodies, Anticalins, designed Ankyrin repeat proteins and others. In an alternative embodiment, $R^1$ and $R^4$ are peptides. In an exemplary embodiment, $R^1$ and $R^4$ are each monoclonal antibodies. In an additional embodiment, $R^1$ and $R^4$ are each double stranded DNA. In a further embodiment, $R^1$ is a double stranded nucleic acid and $R^4$ is an aptamer. In an additional embodiment, $R^1$ is an antibody and $R^4$ is an aptamer. In another additional embodiment, $R^1$ is an antibody and $R^4$ is a double stranded DNA.

In an additional embodiment for molecular biosensors having formula (I), exemplary linkers, $R^2$ and $R^5$, will functionally keep $R^3$ and $R^6$ in close proximity such that when $R^1$ and $R^4$ each bind to the target molecule, $R^8$ and $R^9$ associate in a manner such that a detectable signal is produced. $R^2$ and $R^5$ may each be a nucleotide sequence from about 10 to about 100 nucleotides in length. In one embodiment, $R^2$ and $R^5$ are from 10 to about 25 nucleotides in length. In another embodiment, $R^2$ and $R^5$ are from about 25 to about 50 nucleotides in length. In a further embodiment, $R^2$ and $R^5$ are from about 50 to about 75 nucleotides in length. In yet another embodiment, $R^2$ and $R^5$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^2$ and $R^5$ are comprised of DNA bases. In another embodiment, $R^2$ and $R^5$ are comprised of RNA bases. In yet another embodiment, $R^2$ and $R^5$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^5$ may be nucleotide mimics. Examples of nucleotide mimics may include locked nucleic acids (LNA), peptide nucleic acids (PNA), and phosphorodiamidate morpholine oligomers (PMO). Alternatively, $R^2$ and $R^5$ may be a bifunctional chemical linker, or a polymer of bifunctional chemical linkers. In one embodiment the bifunctional chemical linker is heterobifunctional. Suitable heterobifunctional chemical linkers may include sulfoSMCC (sulfosuccinimidyl-4-(N-maleimidomethyl)cyclohexane-1-carboxylate), and lc-SPDP (N-succinimidyl-6-(3'-(2-pyridyldithio)-propionamido)-hexanoate). In another embodiment the bifunctional chemical linker is homobifunctional. Suitable homobifunctional linkers may include disuccinimidyl suberate, disuccinimidyl glutarate, and disuccinimidyl tartrate. Additional suitable linkers may include the phosphoramidate form of Spacer 18 comprised of polyethylene glycol. In one embodiment, $R^2$ and $R^5$ are from 0 to about 500 angstroms in length. In another embodiment, $R^2$ and $R^5$ are from about 20 to about 400 angstroms in length. In yet another embodiment, $R^2$ and $R^5$ are from about 50 to about 250 angstroms in length.

In a further embodiment for molecular biosensors having formula (I), $R^3$ comprises $R^7$ and $R^8$, and $R^6$ comprises $R^9$. Generally speaking, except for $R^8$ and $R^9$, $R^3$ and $R^6$ are not complementary. $R^8$ and $R^9$ are nucleotide sequences that are complementary to each other such that they preferably do not associate unless $R^1$ and $R^4$ bind to separate epitopes on a target molecule. When $R^1$ and $R^4$ bind to separate epitopes of a target molecule, $R^8$ and $R^9$ are brought into relative proximity resulting in an increase in their local concentration, which drives the association of $R^8$ and $R^9$.

To ensure that $R^8$ and $R^9$ only associate when $R^1$ and $R^4$ bind to separate epitopes of a target, $R^8$ and $R^9$ generally have a length such that the free energy of association is from about −5 to about −12 kcal/mole at a temperature from about 21° C. to about 40° C. and at a salt concentration from about 1 mM to about 100 mM. In other embodiments, the free energy of association between $R^8$ and $R^9$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^8$ and $R^9$ may range from about 4 to about 20 nucleotides in length. In other embodiments, $R^8$ and $R^9$ may be about 4, about 5, about 6, about 7, about 8, about 9, about 10, about 11, about 12, about 13, about 14, about 15, about 16, about 17, about 18, about 19, or greater than about 10 nucleotides in length.

In some embodiments, $R^3$ comprises $R^7$—$R^8$, such that $R^7$ is located 5' to $R^8$. In other embodiments, $R^3$ comprises $R^8$—$R^7$, such that $R^8$ is located 5' to $R^7$.

In an exemplary embodiment, $R^8$ and $R^9$ are at the 3' ends of $R^3$ and $R^6$, such that association of $R^8$ and $R^9$ forms a complex where the 3' ends can be extended using $R^3$ and $R^6$ as a template to form a double-stranded nucleotide sequence comprising $R^7$. Polymerases suitable for extending $R^8$ and $R^9$ are known in the art. For example, non-limiting examples of nucleotide polymerases suitable for extending nucleic acid sequences of the invention may include Bsu DNA Polymerase, DNA Polymerase I (*E. coli*), DNA Polymerase I Large (Klenow) Fragment, Klenow Fragment (3'→5' exo-), phi29 DNA Polymerase, T4 DNA Polymerase, T7 DNA Polymerase (unmodified), or any of the thermophilic polymerases, such as the full length or large fragment of Bst DNA Polymerase, Taq DNA Polymerase, 9° $N_m$ DNA Polymerase, Crimson Taq DNA Polymerase, Deep VentR™ (exo-) DNA Polymerase, Deep VentR™ DNA Polymerase, DyNAzyme™ EXT DNA Polymerase, DyNAzyme™ II Hot Start DNA Polymerase, Hemo KlenTaq™, Phusion® High-Fidelity DNA Polymerase, Sulfolobus DNA Polymerase IV, Therminator™ DNA Polymerase, VentR® DNA Polymerase.

Generally speaking, for molecular biosensors having formula (I) $R^3$ comprises at least one restriction endonuclease recognition site. In some embodiments, however, $R^3$ may comprise more than one restriction endonuclease recognition site. For instance, $R^3$ may comprise at least two, three, four, or five endonuclease recognition sites. Similarly, $R^6$ may comprise at least one, two, three, four or five endonuclease recognition sites.

Typically, a restriction enzyme recognizing a restriction enzyme recognition site cannot cleave or nick a single stranded nucleotide sequence. Association of the epitope binding agents with a target molecule and the subsequent extension of the 3' ends of $R^8$ and $R^9$ in the presence of a polymerase forms a double-stranded endonuclease recognition site that may be cleaved or nicked by a restriction endonuclease. As is commonly known by persons skilled in the art, restriction endonucleases may hydrolyze both strands of the nucleic acid duplex to cleave the nucleic acid duplex, or hydrolyze one of the strands of the nucleic acid duplex, thus producing double-stranded nucleic acid molecules that are "nicked", rather than cleaved. In preferred embodiments of molecular biosensors having formula (I), $R^7$ comprises an endonuclease recognition sequence for a nicking restriction enzyme. A nicking restriction endonuclease may hydrolyze the bottom or the top strand of a nucleic acid duplex. By way of non-limiting example, recognition sites for nicking restriction enzymes may include Nt.BstNBI, Nb.BsrD, Nb.BtsI, Nt.AlwI, Nb.BbvCI, Nt.BbvC and Nb.BsmI.

In each of the foregoing embodiments for molecular biosensors having formula (I), the first nucleic acid construct, $R^1$—$R^2$—$R^3$ and the second nucleic acid construct, $R^4$—$R^5$—$R^6$, may optionally be attached to each other by a linker $R^{LA}$ to create tight binding bivalent ligands. Typically, the attachment is by covalent bond formation. Alternatively, the attachment may be by non covalent bond formation. In one embodiment, $R^{LA}$ attaches $R^1$ of the first nucleic acid construct to $R^4$ of the second nucleic acid construct to form a molecule comprising:

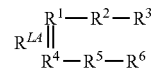

In a further embodiment, $R^{LA}$ attaches $R^2$ of the first nucleic acid construct to R5 of the second nucleic acid construct to form a molecule comprising:

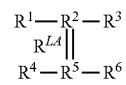

In yet another embodiment, $R^{LA}$ attaches $R^3$ of the first nucleic acid construct to $R^7$ of the second nucleic acid construct to form a molecule comprising:

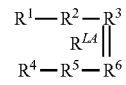

Generally speaking, $R^{LA}$ may be a nucleotide sequence from about 10 to about 100 nucleotides in length. The nucleotides comprising $R^{LA}$ may be any of the nucleotide bases in DNA or RNA (A, C, T, G in the case of DNA, or A, C, U, G in the case of RNA). In one embodiment, $R^{LA}$ is comprised of DNA bases. In another embodiment, $R^{LA}$ is comprised of RNA bases. In yet another embodiment, $R^{LA}$ is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^{LA}$ is comprised of nucleotide mimics. Examples of nucleotide mimics may include locked nucleic acids (LNA), peptide nucleic acids (PNA), and phosphorodiamidate morpholine oligomers (PMO). Alternatively, $R^{LA}$ may be a bifunctional chemical linker or a polymer of bifunctional chemical linkers. In one embodiment the bifunctional chemical linker is heterobifunctional. Suitable heterobifunctional chemical linkers may include sulfoS-MCC (Sulfosuccinimidyl-4-(N-maleimidomethyl)cyclohexane-1-carboxylate), and lc-SPDP (N-Succinimidyl-6-(3'-(2-PyridylDithio)-Propionamido)-hexanoate). In another embodiment, the bifunctional chemical linker is homobifunctional. Suitable homobifunctional linkers may include disuccinimidyl suberate, disuccinimidyl glutarate, and disuccinimidyl tartrate. An exemplary $R^{LA}$ is the phosphoramidate form of Spacer 18 comprised of polyethylene glycol. In one embodiment, $R^{LA}$ is from about 1 to about 500 angstroms in length. In another embodiment, $R^{LA}$ is from about 20 to about 400 angstroms in length. In yet another embodiment, $R^{LA}$ is from about 50 to about 250 angstroms in length.

(b) Means of Detection

As discussed above, when $R^8$ and $R^9$ are extended in the presence of a polymerase, the newly synthesized double-stranded endonuclease recognition sequence may be nicked by a nicking restriction endonuclease that recognizes the double-stranded restriction enzyme recognition site. A DNA polymerase may then extend a second nucleic acid from the nick, thereby displacing the first nicked strand to form a displaced strand. The second extended strand may then be nicked, repeating the extension and displacement steps such that multiple copies of the displaced strand are produced, thereby amplifying the signal from the biosensor. The displaced strand may then be detected via several different methods. Three such methods are detailed below.

i. Double-Stranded Nucleic Acid Stains

In some embodiments, a displaced strand may be detected and/or quantitated by contacting a displaced strand with a complementary nucleic acid sequence. The resulting double-stranded nucleotide sequence may be detected using nucleic acid staining methods specific for double-stranded sequences. Non-limiting examples of nucleic acid stains that may be used for detecting double-stranded nucleotide sequences may include ethidium bromide, thiazole orange, propidium iodide, DAPI, Hoechst dyes, acridine orange, 7-AAD, LDS 751, hydroxystilbamidine, and cyanine dyes such as TOTO-1, POPO-1, BOBO-1, YOYO-1, JOJO-1, LOLO-1, POPO-3, YOYO-3, TOTO-3, BOBO-3, PicoGreen, SYBR Gold, SYBR Green I and SYBR Green II.

ii. Type IIS Endonuclease Construct

In another embodiment, a displaced strand may be detected and/or quantitated by associating with a Type IIS endonuclease nucleic acid construct. The nucleic acid construct may generally comprise two strands, where the first strand comprises $R^{10}$—$R^{12}$—$R^{14}$ and the second strand comprises $R^{11}$—$R^{13}$. $R^{14}$ is complementary to the displaced strand, and when associated with a displaced strand, comprises a Type IIS endonuclease recognition site. $R^{12}$ is complementary to $R^{13}$, and together, $R^{12}$ and $R^{13}$ comprise a cleavage site for a Type IIS endonuclease. $R^{12}$ and $R^{13}$ are of such a length that the two strands (i.e. $R^{10}$—$R^{12}$—$R^{14}$ and $R^{11}$—$R^{13}$) stay hybridized in the absence of the displaced strand. $R^{10}$ and $R^{11}$ comprise a detection means, such that when $R^{12}$ and $R^{13}$ are cleaved by a Type IIS endonuclease, $R^{10}$ and $R^{11}$ are released from the Type IIS endonuclease construct and produce a detectable signal. Suitable detection means for $R^{10}$ and $R^{11}$ may comprise fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes. (See FIG. 1 E2.)

iii. Linker Construct

In some embodiments, a displaced strand may be detected by a linker construct. Usually, a linker construct comprises $R^{15}$—$R^{16}$—$R^{17}$—$R^{18}$—$R^{19}$—$R^{20}$—$R^{21}$. $R^{18}$ is a nucleotide sequence that is complementary to the displaced strand, and together with the displaced strand, comprises an endonuclease recognition site. $R^{17}$ and $R^{19}$ are linkers, and may be defined as $R^2$ and $R^5$ above. $R^{16}$ and $R^{20}$ are complementary nucleic acid sequences, and may be defined as $R^8$ and $R^9$ above. $R^{15}$ and $R^{21}$ comprise a detection means, and may be defined as $R^{10}$ and $R^{11}$ above. (See FIG. 1 E3)

When $R^{18}$ binds to a displaced strand, a double-stranded restriction endonuclease recognition site is formed. In the presence of a restriction endonuclease, $R^{18}$ and the displaced strand are cleaved at the endonuclease recognition site. This destabilizes the association of $R^{16}$ and $R^{20}$, resulting in the separation of $R^{15}$ and $R^{21}$. This separation results in a detectable and quantifiable change in signal intensity.

II. Three-Component Molecular Biosensors

Another aspect of the invention encompasses a three-component biosensor capable of signal amplification. In a three-component embodiment, analogous to a two-component sensor, detection of a target molecule typically involves target-molecule induced co-association of two epitope-binding agent constructs that each recognize distinct epitopes on the target molecule. Unlike the two-component embodiment, however, the epitope-binding agent constructs each comprise single stranded nucleic acid sequences that are complementary to two distinct regions of the oligonucleotide construct, as opposed to being complementary to each other (as in the two-component sensor). Co-association of the two epitope-binding agent constructs with a target molecule results in hybridization of each single stranded nucleic acid sequence to the oligonucleotide construct. This tripartite construct comprised of the two single stranded nucleic acid sequences and the oligonucleotide construct reconstitutes a restriction endonuclease recognition site. The endonuclease recognition site may be cleaved in the presence of a restriction endonuclease. Such cleavage destabilizes the association of the single stranded nucleic acid sequences and the (now cleaved) oligonucleotide construct, releasing the single stranded nucleic acid sequences. The single stranded nucleic acid sequences may then bind to another oligonucleotide construct, repeating the cleavage cycle and therefore amplifying the biosensor signal. Importantly, the oligonucleotide construct is capable of producing a detectable signal when cleaved.

In certain embodiments, the three-component molecular biosensor will comprise a solid support. In alternative embodiments, the three-component molecular biosensor will not comprise a solid support. Both of these embodiments are discussed in more detail below. In some embodiments, a three-component molecular biosensor may comprise a plurality of oligonucleotide constructs (e.g. $R^7$—$R^8$ or $R^7$—$R^8$—$R^9$).

(a) Three Component Molecular Biosensors Comprising a Solid Support

In one embodiment, a three-component molecular biosensor will comprise an oligonucleotide construct attached to a solid support. Generally speaking, co-association of the two epitope-binding agent constructs with a target molecule results in hybridization of each single stranded nucleic acid sequence to the oligonucleotide construct, producing a tripartite double-stranded nucleic acid molecule that contains a restriction endonuclease recognition site. In the presence of a restriction endonuclease, the oligonucleotide construct may be cleaved to release a signaling molecule from the solid support. (See, for instance, FIG. 3)

For example, in some embodiments the three-component molecular biosensor comprises at least three constructs, which together have formula (II):

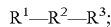

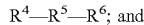

 (II)

wherein:
$R^1$ is an epitope-binding agent that binds to a first epitope on a target molecule;
$R^2$ is a flexible linker attaching $R^1$ to $R^3$;
$R^3$ and $R^6$ are a first pair of nucleotide sequences that are complementary to two distinct regions on $R^8$;
$R^5$ is a flexible linker attaching $R^4$ to $R^6$;
$R^4$ is an epitope-binding agent that binds to a second epitope on a target molecule;
$R^8$ is a nucleotide construct comprising a first region that is complementary to $R^3$ and a second region that is complementary to $R^6$, such that when $R^3$ and $R^6$ associated with $R^8$, an endonuclease restriction site is reconstituted;
$R^7$ is a signaling molecule; and
$R^9$ is a solid support.

The choice of epitope binding agents, $R^1$ and $R^4$, in molecular biosensors having formula (II) can and will vary depending upon the particular target molecule. By way of example, when the target molecule is a protein, $R^1$ and $R^4$ may be an aptamer, or antibody. By way of further example, when $R^1$ and $R^4$ are double stranded nucleic acid the target molecule is typically a macromolecule that binds to DNA or a DNA binding protein. In general, suitable choices for $R^1$ and $R^4$ will include two agents that each recognize distinct epitopes on the same target molecule. In certain embodiments, however, it is also envisioned that $R^1$ and $R^4$ may recognize distinct epitopes on different target molecules. Non-limiting examples of suitable epitope binding agents, depending upon the target molecule, may include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion. In an exemplary embodiment, $R^1$ and $R^4$ are each aptamers having a sequence ranging in length from about 20 to about 110 bases. In another embodiment, $R^1$ and $R^4$ are each antibodies selected from the group consisting of polyclonal antibodies, ascites, Fab fragments, Fab' fragments, monoclonal antibodies, humanized antibodies, chimeric antibodies, and single-chain antibodies. In an alternative embodiment, $R^1$ and $R^4$ are peptides. In a preferred embodiment, $R^1$ and $R^4$ are each monoclonal antibodies. In an additional embodiment, $R^1$ and $R^4$ are each double stranded DNA. In a further embodiment, $R^1$ is a double stranded nucleic acid and $R^4$ is all aptamer. In an additional embodiment, $R^1$ is an antibody and $R^4$ is an aptamer. In another additional embodiment, $R^1$ is an antibody and $R^4$ is a double stranded DNA.

In an additional embodiment for molecular biosensors having formula (II), exemplary linkers, $R^2$ and $R^5$, will functionally keep $R^3$ and $R^6$ in appropriate proximity such that when $R^1$ and $R^4$ each bind to the target molecule, $R^3$ and $R^6$ associate with $R^8$ producing a detectable signal. $R^2$ and $R^5$ may each be a nucleotide sequence from about 10 to about 100 nucleotides in length. In one embodiment, $R^2$ and $R^5$ are from about 10 to about 25 nucleotides in length. In another embodiment, $R^2$ and $R^5$ are from about 25 to about 50 nucleotides in length. In a further embodiment, $R^2$ and $R^5$ are from about 50 to about 75 nucleotides in length. In yet another embodiment, $R^2$ and $R^5$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^2$ and $R^5$ are comprised of DNA bases. In another embodiment, $R^2$ and $R^5$ are comprised of RNA bases. In yet another embodiment, $R^2$ and $R^5$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^5$ may be nucleotide mimics. Examples of nucleotide mimics may include locked nucleic acids (LNA), peptide nucleic acids (PNA), and phosphorodiamidate morpholine oligomers (PMO).

Alternatively, $R^2$ and $R^5$ may be a bifunctional chemical linker or a polymer of bifunctional chemical linkers. In one embodiment the bifunctional chemical linker is heterobifunctional. Suitable heterobifunctional chemical linkers may include sulfoSMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers may include disuccinimidyl suberate, disuccinimidyl glutarate, and disuccinimidyl tartrate. Additional suitable linkers may include the phosphoramidate form of Spacer 18 comprised of polyethylene glycol. In one embodiment, $R^2$ and $R^5$ are from 0 to about 500 angstroms in length. In another embodiment, $R^2$ and $R^5$ are from about 20 to about 400 angstroms in length. In yet another embodiment, $R^2$ and $R^5$ are from about 50 to about 250 angstroms in length.

$R^7$ of formula (II) is a signaling molecule. Suitable signaling molecules are known in the art. Non-limiting examples may include luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

For molecular biosensors having formula (II), $R^8$ comprises a first region that is complementary to $R^6$, and a second region that is complementary to $R^3$. $R^8$ may be from about 8 to about 100 nucleotides in length. In other embodiments, $R^8$ is from about 10 to about 15 nucleotides in length, or from about 15 to about 20 nucleotides in length, or from about 20 to about 25 nucleotides in length, or from about 25 to about 30 nucleotides in length, or from about 30 to about 35 nucleotides in length, or from about 35 to about 40 nucleotides in length, or from about 40 to about 45 nucleotides in length, or from about 45 to about 50 nucleotides in length, or from about 50 to about 55 nucleotides in length, or from about 55 to about 60 nucleotides in length, or from about 60 to about 65 nucleotides in length, or from about 65 to about 70 nucleotides in length, or from about 70 to about 75 nucleotides in length, or from about 75 to about 80 nucleotides in length, or from about 80 to about 85 nucleotides in length, or from about 85 to about 90 nucleotides in length, or from about 90 to about 95 nucleotides in length, or greater than about 95 nucleotides in length.

When $R^3$ and $R^6$ associate with $R^8$, a tripartite double-stranded DNA molecule is formed that contains a restriction endonuclease recognition sequence. In the presence of a restriction endonuclease, $R^8$ is cleaved, releasing $R^7$ from the solid support $R^9$. In an exemplary embodiment, $R^3$ and $R^6$ do not form a stable complex with $R^8$ after $R^8$ is cleaved, freeing $R^3$ and $R^6$ to bind to another $R^8$ and repeat the cleavage cycle. This amplifies the biosensor signal.

In an exemplary embodiment, $R^8$ will comprise formula (III):

$$R^{10}\text{—}R^{11}\text{—}R^{12}\text{—}R^{13} \quad (III)$$

wherein:
$R^{10}$ and $R^{13}$ are single-stranded nucleotide sequences not complementary to any of $R^1$, $R^2$, $R^3$, $R^4$, $R^5$, or $R^6$;
$R^{11}$ is a nucleotide sequence complementary to $R^3$; and
$R^{12}$ is a nucleotide sequence that is complementary to $R^6$.

In some embodiments, $R^{10}$ and $R^{13}$ may independently be from about 0 to about 20 nucleotides in length. In other embodiments, $R^{10}$ and $R^{13}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length.

Generally speaking, $R^{11}$ and $R^{12}$ have a length such that the free energy of association between $R^{11}$ and $R^3$ and $R^{12}$ and $R^6$ is from about −5 to about −12 kcal/mole at a temperature from about 21° C. to about 40° C. and at a salt concentration from about 1 mM to about 100 mM. In other embodiments, the free energy of association between $R^{11}$ and $R^3$ and $R^{12}$ and $R^6$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{11}$ and $R^{12}$ may range from about 4 to about 20 nucleotides in length. In other embodiments, $R^{11}$ and $R^{12}$ may be about 4, about 5, about 6, about 7, about 8, about 9, about 10, about 11, about 12, about 13, about 14, about 15, about 16, about 17, about 18, about 19, or greater than about 10 nucleotides in length.

In one embodiment, when $R^8$ comprises formula (III), the cleavage site of the restriction endonuclease recognition sequence produced by the association of $R^3$ and $R^6$ with $R^8$ is located between $R^{11}$ and $R^{12}$. In this manner, in the presence of a suitable restriction endonuclease, $R^8$ will be cleaved between $R^{11}$ and $R^{12}$, but $R^3$ and $R^6$ remain intact. Suitable restriction endonuclease recognition sequences are recognized by restriction enzymes that cleave double stranded nucleic acid, but not single stranded nucleic acid. Such enzymes and the corresponding recognition sites are known in the art. By way of non-limiting example, these enzymes may include AccI, AgeI, BamHI, BglI, BglII, BsiWI, BstBI, ClaI, CviQI, DdeI, DpnI, DraI, EagI, EcoRI, EcoRV, FseI, FspI, HaeII, HaeIII, HhaI, HincII, HinDIII, HpaI, HpaII, KpnI, KspI, MboI, MfeI, NaeI, NarI, NcoI, NdeI, NheI, NotI, PhoI, PstI, PvuI, PvuII, SacI, SacI, SalI, SbfI, SmaI, SpeI, SphI, StuI, TaqI, TliI, TfiI, XbaI, XhoI, XmaI, XmnI, and ZraI.

In another exemplary embodiment, $R^8$ will comprise formula (IV):

$$R^{10}\text{—}R^{11}\text{—}R^{12}\text{—}R^{13}\text{—}R^{14}\text{—}R^{15} \quad (IV)$$

wherein:
$R^{11}$, $R^{12}$, $R^{13}$, and $R^{14}$ are single stranded oligonucleotide sequences not complementary to each other or any of $R^1$, $R^2$, $R^3$, $R^4$, $R^5$, or $R^6$;
$R^{10}$ and $R^{15}$ are double-stranded nucleic acid sequences;
$R^{12}$ is a nucleotide sequence complementary to $R^3$; and
$R^{13}$ is a nucleotide sequence that is complementary to $R^6$.

$R^{11}$ and $R^{14}$ may independently be from about 0 to about 20 nucleotides in length. In other embodiments, $R^{11}$ and $R^{14}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;

$R^{10}$ and $R^{15}$ may independently be from about 0 to about 20 base pairs in length. In other embodiments, $R^{10}$ and $R^{15}$ may independently be from about 2 to about 4 base pairs in length, or from about 4 to about 6 base pairs in length, or from about 6 to about 8 base pairs in length, or from about 8 to about 10 base pairs in length, or from about 10 to about 12 base pairs in length, or from about 12 to about 14 base pairs in length, or from about 14 to about 16 base pairs in length, or from about 16 to about 18 base pairs in length, or from about 18 to about 20 base pairs in length, or greater than about 20 base pairs in length;

$R^{12}$ and $R^{13}$ generally have a length such that the free energy of association between $R^{12}$ and $R^3$ and $R^{13}$ and $R^6$ is from about −5 to about −12 kcal/mole at a temperature from about 21° C. to about 40° C. and at a salt concentration from about 1 mM to about 100 mM. In other embodiments, the free energy of association between $R^{12}$ and $R^3$ and $R^{13}$ and $R^6$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{12}$ and $R^{13}$ may range from about 4 to about 20 nucleotides in length. In other embodiments, $R^{12}$ and $R^{13}$ may be about 4, about 5, about 6, about 7, about 8, about 9, about 10, about 11, about 12, about 13, about 14, about 15, about 16, about 17, about 18, about 19, or greater than about 20 nucleotides in length.

In yet another exemplary embodiment, $R^8$ may comprise formula (V):

$$R^{10}\text{—}R^{11}\text{—}R^{12}\text{—}R^{13}\text{—}R^{14}\text{—}R^{15}\text{—}R^{16} \quad (V)$$

wherein:
$R^{11}$, $R^{12}$, $R^{14}$, $R^{15}$ and $R^{16}$ are single stranded oligonucleotide sequences independently not complementary to each other or any of $R^1$, $R^2$, $R^3$, $R^4$, $R^5$, or $R^6$;

$R^{10}$ and $R^{13}$ are double-stranded nucleic acid sequences; $R^{11}$ is a nucleotide sequence complementary to $R^3$; and $R^{15}$ is a nucleotide sequence that is complementary to $R^6$.

$R^{12}$, $R^{14}$ and $R^{16}$ may independently be from about 0 to about 20 nucleotides in length. In other embodiments, $R^{12}$, $R^{14}$, and $R^{16}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length.

$R^{10}$ and $R^{13}$ may independently be from about 0 to about 20 base pairs in length. In other embodiments, $R^{10}$ and $R^{13}$ may independently be from about 2 to about 4 base pairs in length, or from about 4 to about 6 base pairs in length, or from about 6 to about 8 base pairs in length, or from about 8 to about 10 base pairs in length, or from about 10 to about 12 base pairs in length, or from about 12 to about 14 base pairs in length, or from about 14 to about 16 base pairs in length, or from about 16 to about 18 base pairs in length, or from about 18 to about 20 base pairs in length, or greater than about 20 base pairs in length.

$R^{11}$ and $R^{15}$ generally have a length such that the free energy of association between $R^{11}$ and $R^3$ and $R^{15}$ and $R^6$ is from about −5 to about −12 kcal/mole at a temperature from about 21° C. to about 40° C. and at a salt concentration from about 1 mM to about 100 mM. In other embodiments, the free energy of association between $R^{11}$ and $R^3$ and $R^{15}$ and $R^6$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{11}$ and $R^{15}$ may range from about 4 to about 20 nucleotides in length. In other embodiments, $R^{11}$ and $R^{15}$ may be about 4, about 5, about 6, about 7, about 8, about 9, about 10, about 11, about 12, about 13, about 14, about 15, about 16, about 17, about 18, about 19, or greater than about 10 nucleotides in length.

When $R^8$ comprises formula (IV) or formula (V), a cleavage site of a restriction endonuclease recognition sequence produced by the association of $R^3$ and $R^6$ with $R^8$ may be located within $R^{10}$ for either formula (IV) or formula (V), $R^{15}$ for formula (IV), $R^{13}$ for formula (V), or a combination thereof. Suitable restriction endonuclease recognition sequences for these embodiments are recognized by restriction enzymes that cleave double stranded nucleic acid outside the recognition sequence of the restriction enzyme. Such enzymes and the corresponding recognition and cleavage sites are known in the art. By way of non-limiting example, these sites may include AcuI, AlwI, BaeI, BbsI, BbvI, BccI, BceAI, BcgI, BciVI, BfuAI, BmrI, BpmI, BpuEI, BsaI, BsaXI, BseRI, BsgI, BsmAI, BsmBI, BsmFI, BspCNI, BspMI, BspQI, BtgZI, CspCI, EarI, EciI, EcoP15I, FokI, HgaI, HphI, HpyAV, MboII, MlyI, MmeI, MmeAIII, PleI, SapI, SfaNI.

In some embodiments for molecular biosensors having Formula (IV) or Formula (V), $R^7$ may comprise two signaling molecules, each attached to one strand of a double-stranded nucleotide sequence comprising $R^8$. Cleavage of the restriction enzyme recognition site results in the release and separation of the two signaling molecules, resulting in a detectable and quantifiable change in signal intensity.

Exemplary detections means suitable for use in the molecular biosensors include fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes.

In some embodiments, $R^9$ is a solid support having $R^8$ attached thereto. Non-limiting examples of suitable solid supports may include microtitre plates, test tubes, beads, resins and other polymers, as well as other surfaces either known in the art or described herein. The solid support may be a material that may be modified to contain discrete individual sites appropriate for the attachment or association of the construct and is amenable to at least one detection method. Non-limiting examples of solid support materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. The size and shape of the solid support may also vary without departing from the scope of the invention. A solid support may be planar, a solid support may be a well, i.e. a 384 well plate, or alternatively, a solid support may be a bead or a slide.

$R^8$ may be attached to the $R^9$ in a wide variety of ways, as will be appreciated by those in the art. $R^8$, for example, may either be synthesized first, with subsequent attachment to the solid support, or may be directly synthesized on the solid support. $R^9$ and $R^5$ may be derivatized with chemical functional groups for subsequent attachment of the two. For example, the solid support may be derivatized with a chemical functional group including, but not limited to, amino groups, carboxyl groups, oxo groups or thiol groups. Using these functional groups, the $R^5$ may be attached using functional groups either directly or indirectly using linkers. Alternatively, $R^5$ may also be attached to the surface non-covalently. For example, a biotinylated $R^5$ can be prepared, which may bind to surfaces covalently coated with streptavidin, resulting in attachment. Alternatively, $R^5$ may be synthesized on the surface using techniques such as photopolymerization and photolithography. Additional methods of attaching $R^5$ to a surface and methods of synthesizing nucleic acids on surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2): 155-177, all of which are hereby incorporated by reference in their entirety).

In each of the foregoing embodiments for molecular biosensors having formula (III), the first nucleic acid construct, $R^1$—$R^2$—$R^3$ and the second nucleic acid construct, $R^4$—$R^5$—$R^6$, may optionally be attached to each other by a linker $R^{LA}$ to create tight binding bivalent ligands. Typically, the attachment is by covalent bond formation. Alternatively, the attachment may be by non covalent bond formation. In one embodiment, $R^{LA}$ attaches $R^1$ of the first nucleic acid construct to $R^4$ of the second nucleic acid construct to form a molecule comprising:

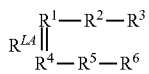

In a further embodiment, $R^{LA}$ attaches $R^2$ of the first nucleic acid construct to $R^5$ of the second nucleic acid construct to form a molecule comprising:

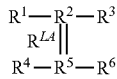

In yet another embodiment, RLA attaches R3 of the first nucleic acid construct to R7 of the second nucleic acid construct to form a molecule comprising:

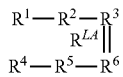

Generally speaking, $R^{LA}$ may be a nucleotide sequence from about 10 to about 100 nucleotides in length. The nucleotides comprising $R^{LA}$ may be any of the nucleotide bases in DNA or RNA (A, C, T, G in the case of DNA, or A, C, U, G in the case of RNA). In one embodiment, $R^{LA}$ is comprised of DNA bases. In another embodiment, $R^{LA}$ is comprised of RNA bases. In yet another embodiment, $R^{LA}$ is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^{LA}$ is comprised of nucleotide mimics. Examples of nucleotide mimics include locked nucleic acids (LNA), peptide nucleic acids (PNA), and phosphorodiamidate morpholine oligomers (PMO). Alternatively, $R^{LA}$ may be a polymer of bifunctional chemical linkers. In one embodiment the bifunctional chemical linker is heterobifunctional. Suitable heterobifunctional chemical linkers include sulfoS-MCC (Sulfosuccinimidyl-4-(N-maleimidomethyl)cyclohexane-1-carboxylate), and lc-SPDP (N-Succinimidyl-6-(3'-(2-PyridylDithio)-Propionamido)-hexanoate). In another embodiment, the bifunctional chemical linker is homobifunctional. Suitable homobifunctional linkers include disuccinimidyl suberate, disuccinimidyl glutarate, and disuccinimidyl tartrate. An exemplary $R^{LA}$ is the phosphoramidate form of Spacer 18 comprised of polyethylene glycol. In one embodiment, $R^{LA}$ is from about 1 to about 500 angstroms in length. In another embodiment, $R^{LA}$ is from about 20 to about 400 angstroms in length. In yet another embodiment, $R^{LA}$ is from about 50 to about 250 angstroms in length.

(b) Three Component Molecular Biosensors without a Solid Support

In an alternative embodiment of the three-component biosensor, the biosensor does not comprise a solid support. For instance, in some embodiments, the three-component molecular biosensor comprises three constructs, which together have formula (VI):

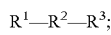

$R^4$—$R^5$—$R^6$; and at least one $R^7$—$R^8$; (VI)

wherein:
$R^1$ is an epitope-binding agent that binds to a first epitope on a target molecule;
$R^2$ is a flexible linker attaching $R^1$ to $R^3$;
$R^3$ and $R^6$ are a first pair of nucleotide sequences that are complementary to two distinct regions on $R^8$;
$R^5$ is a flexible linker attaching $R^4$ to $R^6$;
$R^6$ is an epitope-binding agent that binds to a second epitope on a target molecule;
$R^8$ is a nucleotide construct comprising a first region that is complementary to $R^3$ and a second region that is complementary to $R^6$, such that when $R^3$ and $R^6$ associated with $R^8$, an endonuclease restriction site is reconstituted;
$R^7$ is a signaling molecule.

$R^1$, $R^2$, $R^3$, $R^4$, $R^5$, $R^6$, and $R^7$ may be as defined above for three-component molecular biosensors having formula (II). $R^8$ may be as described in Section (II)(a) above.

In some embodiments for molecular biosensors having Formula (VI), $R^7$ may comprise two signaling molecules, each attached to one strand of a double-stranded nucleotide sequence comprising $R^8$. Cleavage of the restriction enzyme recognition site results in the release and separation of the two signaling molecules, resulting in a detectable and quantifiable change in signal intensity. Exemplary detections means suitable for use in the molecular biosensors include fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes.

III. Methods for Utilizing a Molecular Biosensor

A further aspect of the invention encompasses the use of the molecular biosensors of the invention in several applications. In certain embodiments, the molecular biosensors are utilized in methods for detecting one or more target molecules. In other embodiments, the molecular biosensors may be utilized in kits and for therapeutic and diagnostic applications.

In one embodiment, the molecular biosensors may be utilized for detection of a target molecule. The method generally involves contacting a molecular biosensor of the invention with the target molecule. To detect a target molecule utilizing two-component biosensors, the method typically involves target-molecule induced co-association of two epitope-binding agents (present in the molecular biosensor of the invention) that each recognize distinct epitopes on the target molecule. The epitope-binding agents each comprise complementary oligonucleotides. Co-association of the two epitope-binding agents with the target molecule results in annealing of the two complementary oligonucleotides such that a detectable signal is produced. Typically, the detectable signal is produced by any of the detection means known in the art or as described herein. Alternatively, for three-component biosensors, co-association of the two epitope-binding agent constructs with the target molecule results in hybridization of each signaling oligos to the oligonucleotide construct. Binding of the two signaling oligo to the oligonucleotide construct brings them into proximity such that a detectable signal is produced.

In one particular embodiment, a method for the detection of a target molecule that is a protein or polypeptide is provided. The method generally involves detecting a polypeptide in a sample comprising the steps of contacting a sample with a molecular biosensor of the invention. By way of non-limiting example, the molecular biosensor may comprise two aptamers recognizing two distinct epitopes of a protein, a double stranded polynucleotide containing binding site for DNA binding protein and an aptamer recognizing a distinct epitope of the protein, an antibody and an aptamer recognizing distinct epitopes of the protein, a double stranded polynucleotide containing a binding site for a DNA binding protein and an antibody recognizing a distinct epitope of the protein, two antibodies recognizing two distinct epitopes of the protein, two double stranded polynucleotide fragments recognizing two distinct sites of the protein, two single stranded polynucleotide elements recognizing two distinct sequence elements of another single stranded polynucleotide.

Figure 13:
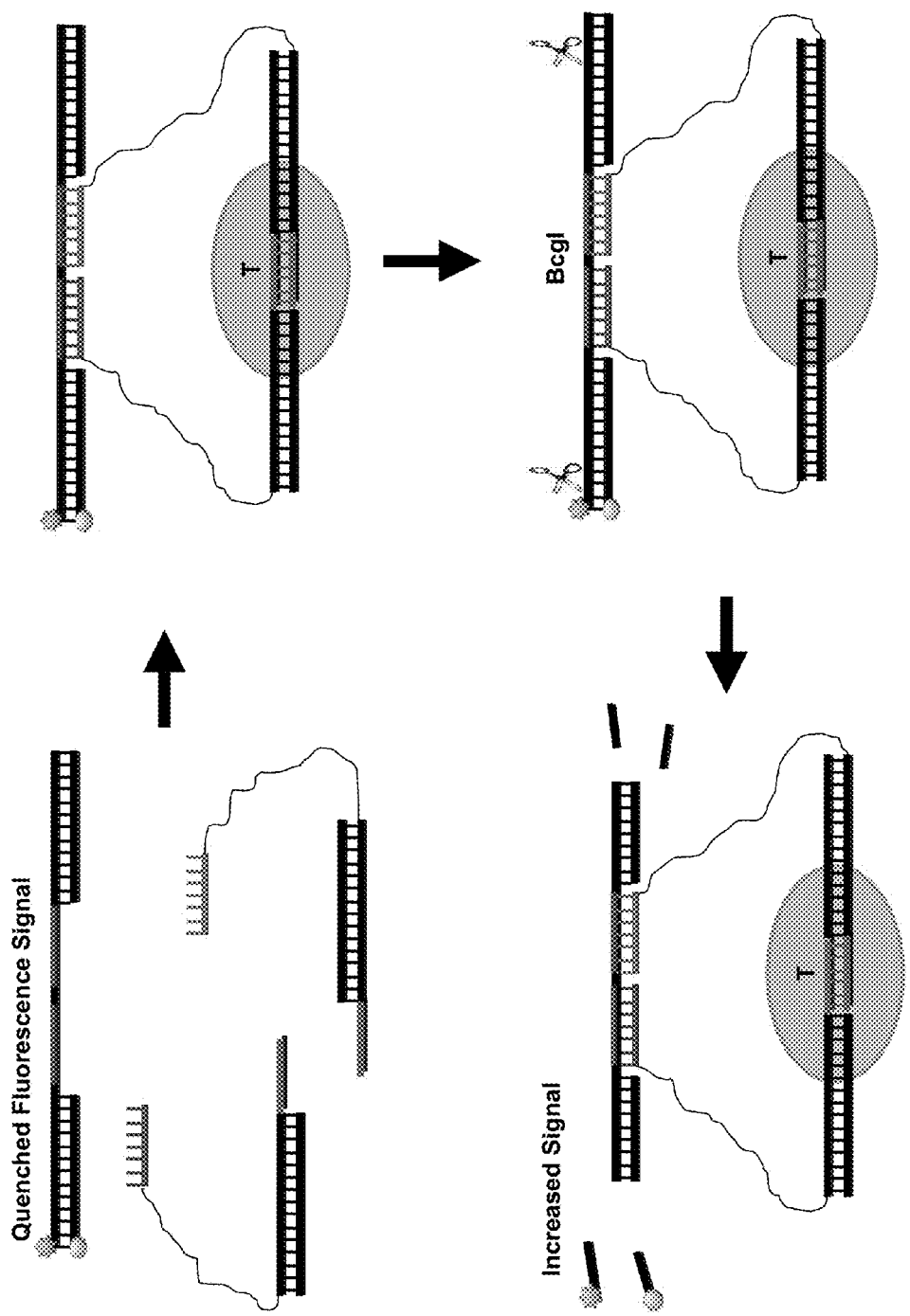
FIG. 13 depicts the use of a three-component molecular biosensor for detection of double-stranded nucleotide sequence binding proteins.
Figure 14:
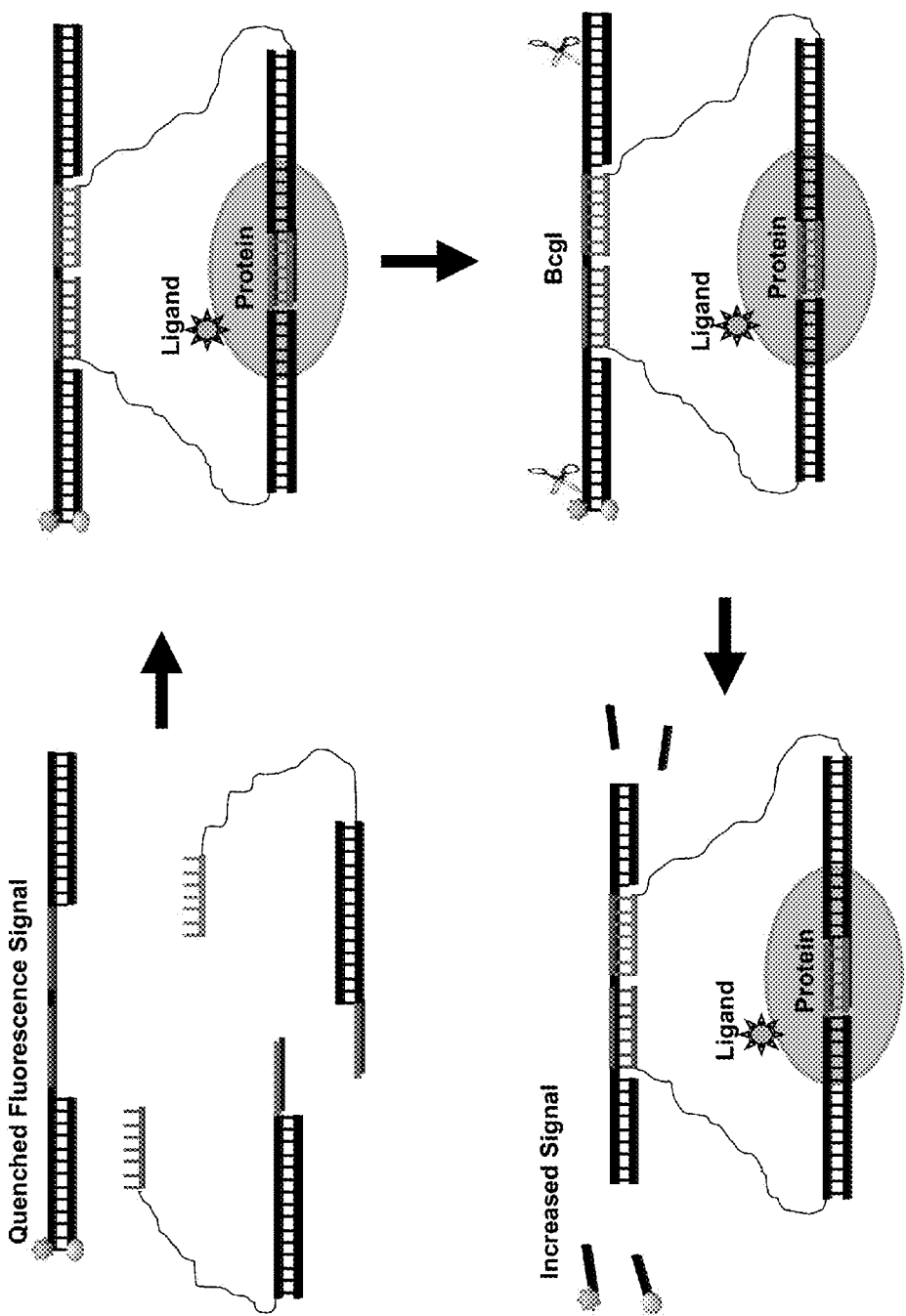
FIG. 14 depicts the use of a three-component molecular biosensor for detection of ligands of double-stranded nucleotide sequence binding proteins.

The molecular biosensor may also detect formation of a protein-polynucleotide complex using a double stranded polynucleotide fragment (containing the binding site of the protein) labeled with a first signaling oligonucleotide and the protein labeled with a second signaling oligonucleotide (FIGS. 13 and 14). Or alternatively, the biosensor may comprise a first polynucleotide fragment with a complementary overhang to a second polynucleotide fragment, such that in the presence of a DNA-binding protein, the first polynucleotide fragment associates with the second polynucleotide fragment to create the DNA-binding protein epitope, which allows association of the DNA-binding protein with the DNA-binding protein epitope. The molecular biosensor may also comprise a molecular biosensor that allows for the direct detection of the formation of a protein-protein complex using two corresponding proteins labeled with signaling oligonucleotides.

In another embodiment, the molecular biosensors may be used to detect a target molecule that is a macromolecular complex in a sample. In this embodiment, the first epitope is preferably on one polypeptide and the second epitope is on another polypeptide, such that when a macromolecular complex is formed, the one and another polypeptides are bought into proximity, resulting in the stable interaction of the first aptamer construct and the second aptamer construct to produce a detectable signal, as described above.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The term "antibody" generally means a polypeptide or protein that recognizes and can bind to an epitope of an antigen. An antibody, as used herein, may be a complete antibody as understood in the art, i.e., consisting of two heavy chains and two light chains, or be selected from a group comprising polyclonal antibodies, ascites, Fab fragments, Fab' fragments, monoclonal antibodies, chimeric antibodies humanized antibodies, and a peptide comprising a hypervariable region of an antibody.

The term "aptamer" refers to a polynucleotide, generally a RNA or a DNA that has a useful biological activity in terms of biochemical activity, molecular recognition or binding attributes. Usually, an aptamer has a molecular activity such as binding to a target molecule at a specific epitope (region). It is generally accepted that an aptamer, which is specific in its binding to any polypeptide, may be synthesized and/or identified by in vitro evolution methods As used herein, "detection method" means any of several methods known in the art to detect a molecular interaction event. The phrase "detectable signal", as used herein, is essentially equivalent to "detection method."

The term "epitope" refers generally to a particular region of a target molecule. Examples include an antigen, a hapten, a molecule, a polymer, a prion, a microbe, a cell, a peptide, polypeptide, protein, a nucleic acid, or macromolecular complex. An epitope may consist of a small peptide derived from a larger polypeptide. An epitope may be a two or three-dimensional surface or surface feature of a polypeptide, protein or macromolecular complex that comprises several non-contiguous peptide stretches or amino acid groups.

The term "epitope binding agent" refers to a substance that is capable of binding to a specific epitope of an antigen, a polypeptide, a nucleic acid, a protein or a macromolecular complex. Non-limiting examples of epitope binding agents include aptamers, thioaptamers, double-stranded DNA sequence, peptides and polypeptides, ligands and fragments of ligands, receptors and fragments of receptors, antibodies and fragments of antibodies, polynucleotides, coenzymes, coregulators, allosteric molecules, peptide nucleic acids, locked nucleic acids, phosphorodiamidate morpholino oligomers (PMO) and ions. Peptide epitope binding agents include ligand regulated peptide epitope binding agents.

The term "epitope binding agent construct" refers to a construct that contains an epitope-binding agent and can serve in a "molecular biosensor" with another molecular biosensor. Preferably, an epitope binding agent construct also contains a "linker," and an "oligo". An epitope binding agent construct can also be referred to as a molecular recognition construct.

The term "target molecule," as used herein, refers to a molecule that may be detected with a biosensor of the invention. By way of non-limiting example, a target may be a biomolecule such as an antigen, a polypeptide, a protein, a nucleic acid, a carbohydrate, or a macromolecular complex thereof. Alternatively, a target may be a hapten, a molecule, a polymer, a prion, a microbe, a cell, or a macromolecular complex thereof.

The term "signaling molecule," as used herein, refers to any substance attachable to a polynucleotide, polypeptide, aptamer, nucleic acid component, or other substrate material, in which the substance is detectable by a detection method. Non-limiting examples of labels applicable to this invention include but are not limited to luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

EXAMPLES

The following examples illustrate various iterations of the invention.

Example 1

Two-Component Molecular Biosensors Comprising a Single Nicking Restriction Endonuclease Recognition Site This example describes a method for the rapid and sensitive detection of a target molecule using a two-component molecular biosensor. This method is based on the target-driven association of two constructs containing epitope-binding agents that recognize two distinct epitopes of a target (FIG. 1). These two epitope-binding agent constructs each comprise a single-stranded nucleotide sequence. Each single-stranded sequence comprises a complementary 3' end sequence, and a restriction endonuclease recognition site. The complementary 3' end sequences are brought into close proximity when the epitope binding agents co-associate with a molecular target, resulting in annealing of the complementary 3' end sequences such that, when the complementary regions are extended by a nucleotide polymerase, a double-stranded nucleic acid comprising a restriction enzyme recognition site is reconstituted. A nicking restriction endonuclease enzyme that recognizes the reconstituted restriction enzyme recognition site nicks one strand of the newly synthesized nucleic acid duplex. A DNA polymerase extends a second nucleic acid thereby displacing the first displaced strand, and producing a displaced single-stranded nucleic acid. The second extended strand is then nicked and the extension/displacement cycle may be repeated to produce multiple copies of the displaced strand, thereby providing a means of amplifying the signal. The produced nicked strand may then be quantified using one of several different methods. Three possible methods are detailed below.

Double-Stranded Nucleic Acid Stains

The displaced DNA strand may be detected by annealing with a complementary nucleic acid sequence, to form double stranded DNA which may be detected using stains that specifically bind double stranded DNA (FIG. 1 E1).

Detection Using a Type IIS Endonuclease Construct

The displaced DNA strand may be detected by annealing to a type IIS endonuclease construct (FIG. 1 E2). The type IIS endonuclease construct comprises a double-stranded DNA region, and a single-stranded DNA region. The single stranded DNA region of the construct is complementary to the displaced DNA strand, such that when the displaced strand associates with the construct, a type IIS endonuclease recognition site is reconstituted. The construct also comprises a detection means, such that when a type IIS endonuclease cleaves the construct, the detection means are released from the construct, and a detectable signal is produced.

Detection Using a Linker Construct

The displaced strand may be detected by annealing to a linker construct (FIG. 1 E3). In general, a linker construct would comprise a double-stranded DNA region, and a single-stranded DNA region. The linker construct also comprises a detection means linked to a pair of complementary oligonucleotides. The pair of complementary oligonucleotides, and the detection means linked to them, are linked to the double-stranded and single-stranded DNA regions through flexible linkers. The single stranded DNA region of the construct is complementary to the displaced DNA strand, such that when the displaced strand associates with the construct, a double-stranded restriction endonuclease recognition site is reconstituted. In the presence of a restriction endonuclease, double-stranded DNA region and the displaced strand are cleaved at the endonuclease site resulting in the separation of the detection means, and a detectable signal is produced.

Example 2

Figure 2:
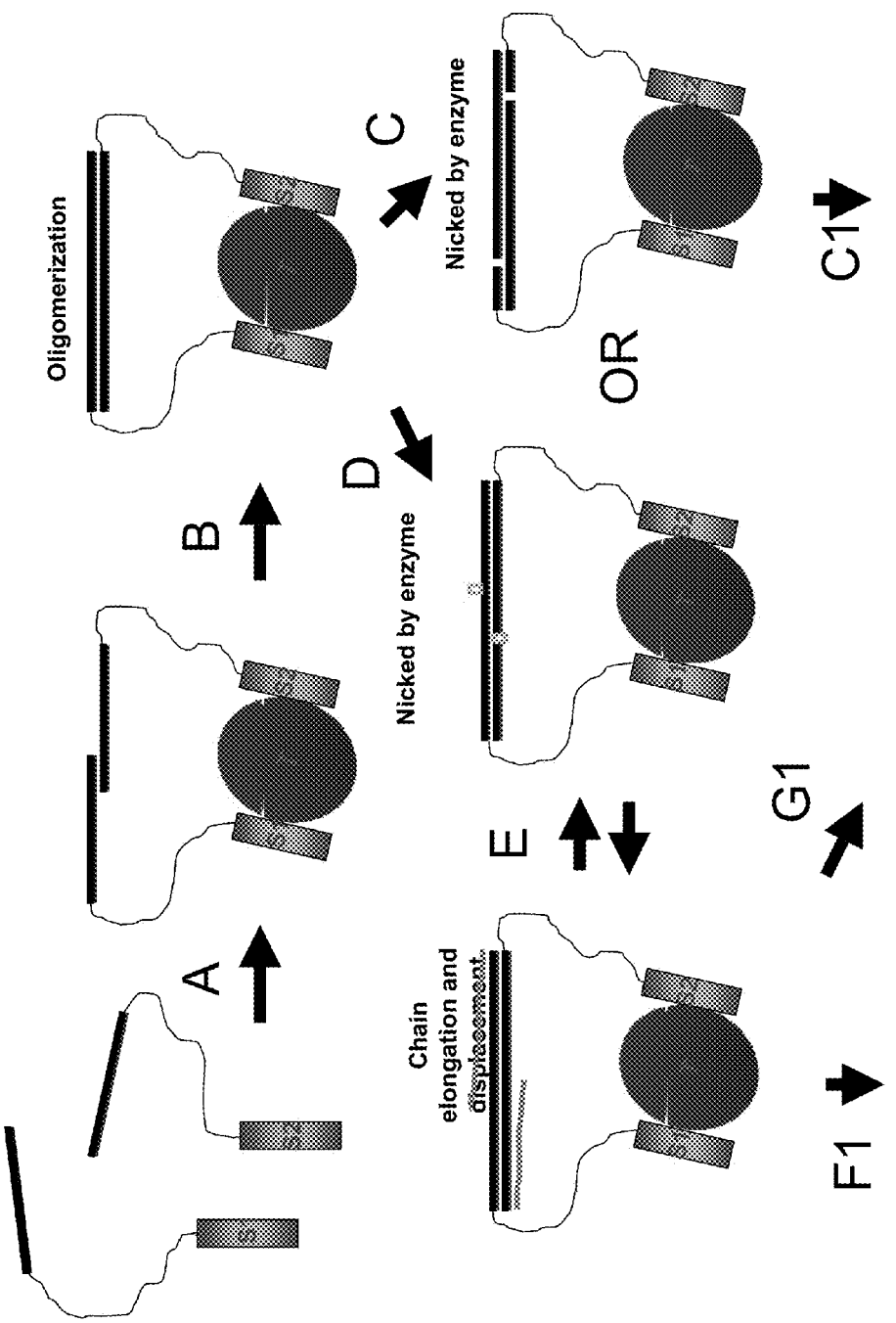
FIG. 2 depicts the overall design and function of a two-component molecular biosensor comprising two nicking sites.
Figure 2:
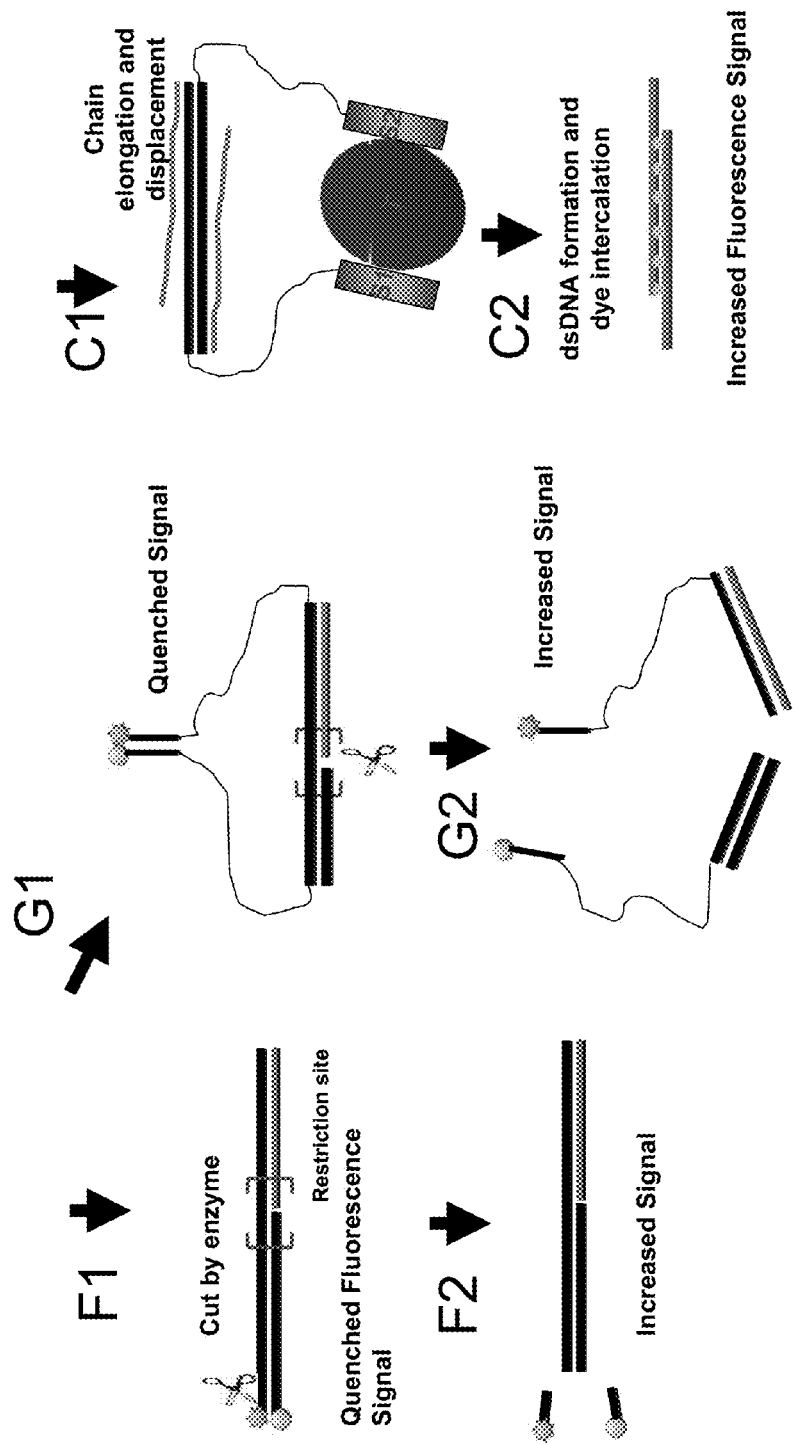

Two Component Molecular Biosensors Comprising Two Nicking Restriction Endonuclease Recognition Sites In an alternative embodiment of the target detection method described in Example 1 above, the single-stranded nucleotide sequences of the epitope-binding agent constructs comprise two restriction enzyme recognition sites (FIG. 2). In some embodiments, the restriction sites may be distal to each other (FIG. 2 C1). In these embodiments, DNA polymerase extends the double-stranded nucleic acid producing two displaced strands. The nicking, and the extension/displacement cycle may be repeated to produce multiple copies of the displaced strands to amplify the signal. The displaced strands produced are complementary, and may be detected using stains that specifically bind double stranded DNA (FIG. 2 C2) as described in Example 1 above.

In other embodiments the restriction endonuclease sites may be proximal to each other. In these embodiments, the displaced strands are not complementary to each other, but may be detected by annealing to type IIS endonuclease constructs (FIG. 2 F1 and F2) or linker constructs (FIGS. 2 G1 and G2) as described in Example 1 above.

Example 3

Validation of Three Component Molecular Biosensor

Figure 3:
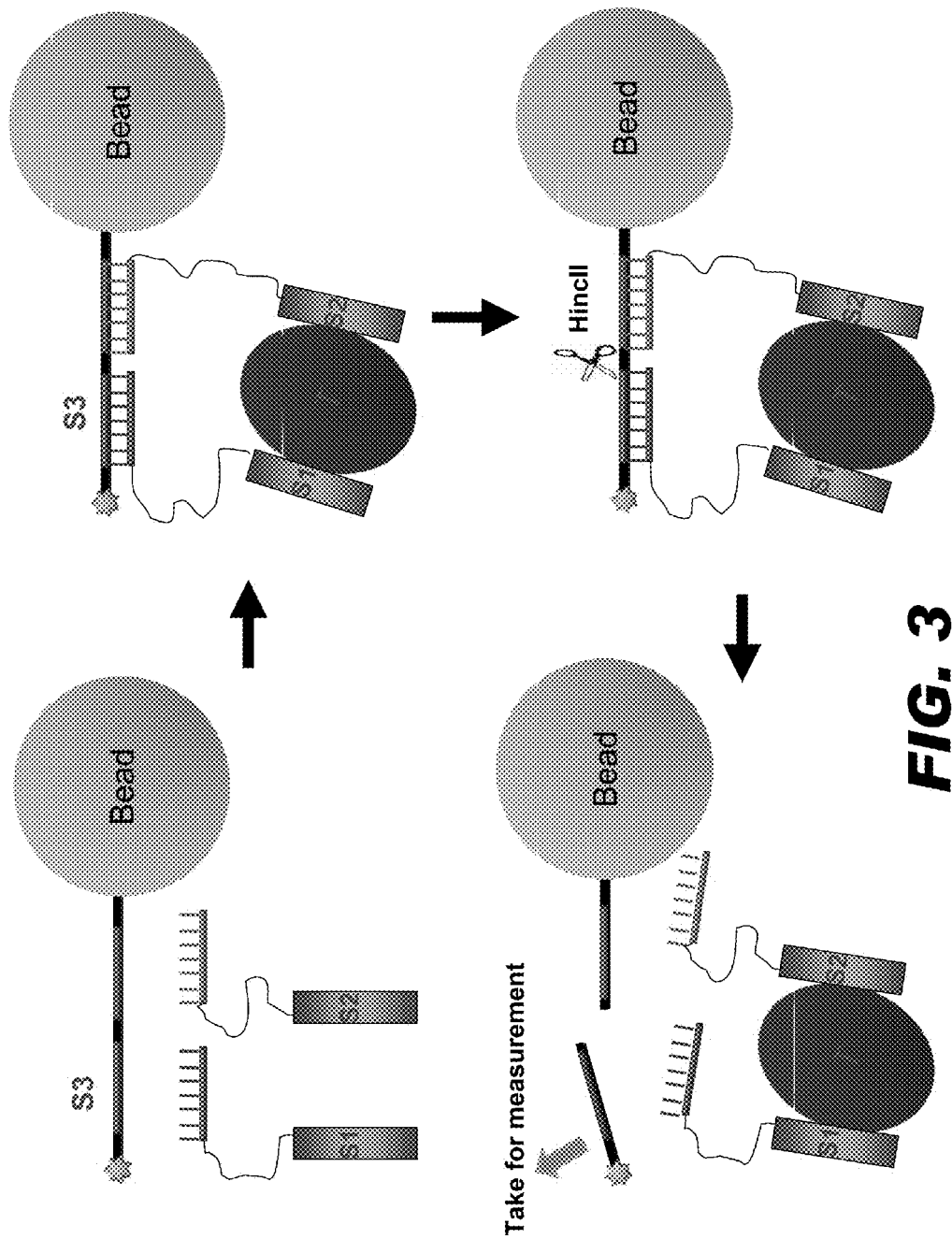
FIG. 3 depicts the overall design and function of a three-component molecular biosensor comprising a signaling oligonucleotide attached to a bead.

This example describes a method for the rapid and sensitive detection of a target molecule using a three-component molecular biosensor (FIG. 3). The three component biosensor comprises two epitope-binding agent constructs and a single-stranded oligonucleotide construct comprising a restriction enzyme recognition site. The oligonucleotide construct is immobilized on a solid support and comprises a signaling molecule. Detection of a target molecule typically involves target-molecule induced co-association of the two epitope-binding agent constructs that each recognizes distinct epitopes on the target molecule. The epitope-binding agent constructs each comprise a single-stranded nucleotide sequence that are not complementary to each other, but are complementary to two distinct regions of an oligonucleotide construct. Co-association of the two epitope-binding agent constructs with the target molecule results in hybridization of single-stranded nucleotide sequences to distinct regions of the oligonucleotide construct. This tripartite construct comprising the two single-stranded nucleic acid sequences and the oligonucleotide construct reconstitutes a restriction endonuclease recognition site. When a restriction endonuclease cleaves the restriction endonuclease site, releasing the signaling molecule from the solid support for measurement.

Figure 4:
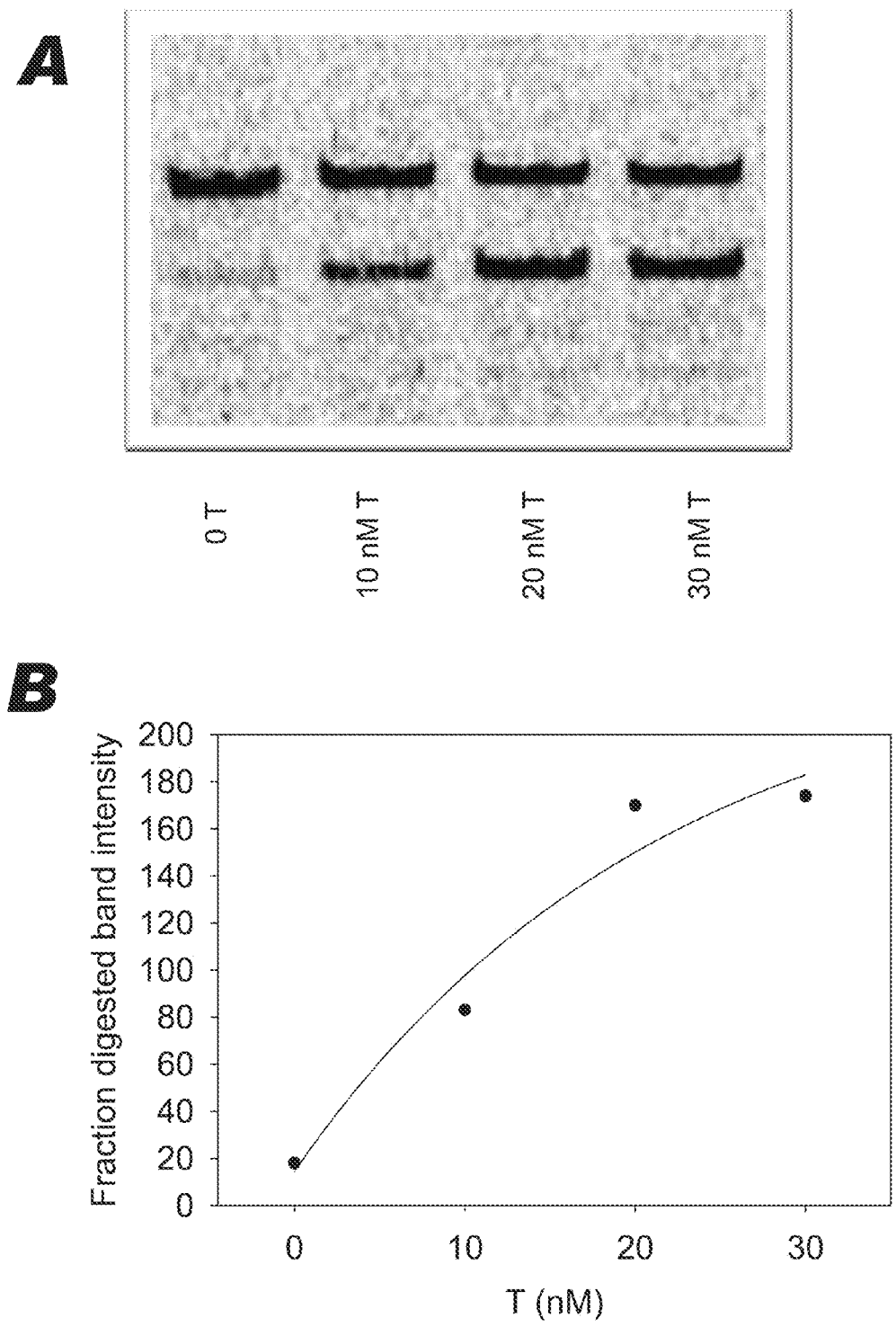
FIG. 4 (A) an agarose gel resolving the digestion products of a three-component molecular biosensor attached to a bead, when increasing concentrations of the target are added. (B) Quantification results of digestion products in (A) using a densitometer.

To validate the assay described, epitope binding agent constructs were incubated with 0, 10, 20 and 30 nM concentrations of target molecule in the presence of an oligonucleotide construct in a master mix containing the restriction enzyme HincII. The reaction was then loaded onto an agarose gel, and the products of the restriction digestion reaction resolved. The results show that in the absence of target molecule, only 20% of the oligonucleotide construct was digested by the HincII enzyme. Adding increasing concentrations of the target molecule resulted in increasing digestion of the oligonucleotide construct (FIG. 4).

Example 4

Three Component Molecular Biosensor Immobilized on Magnetic Beads

Figure 5:
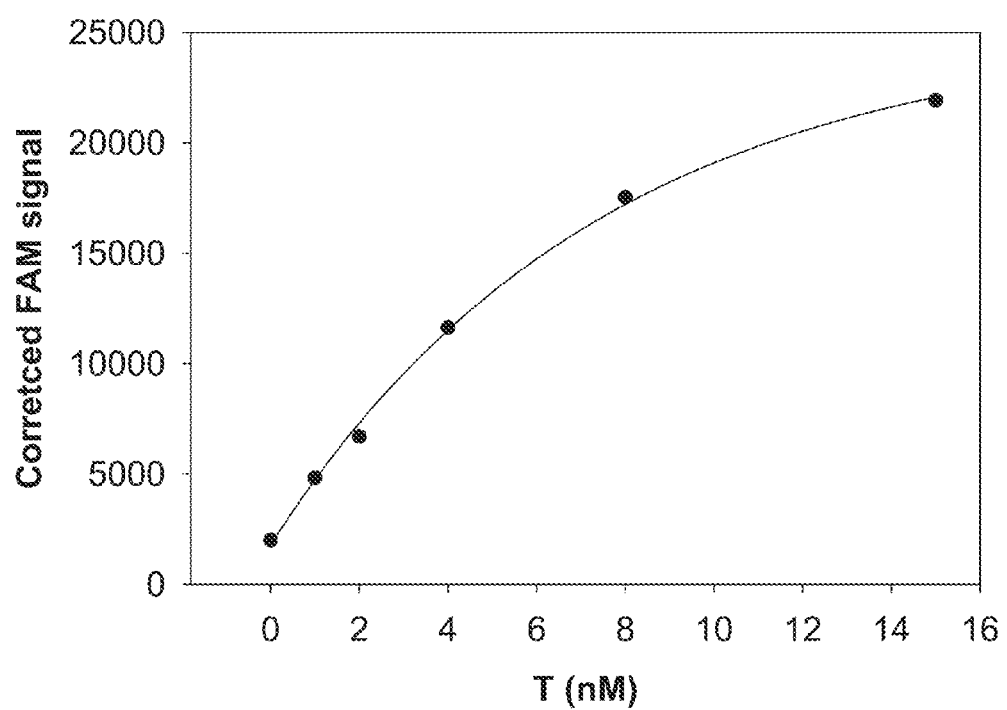
FIG. 5 depicts FAM signal increase in supernatant when increasing concentrations of the target are added to a three-component molecular biosensor attached to a bead.

In this example, the oligonucleotide construct described in Example 3 was labeled with FAM, then conjugated with biotin and immobilized on streptavidin magnetic beads (SMB). The oligonucleotide construct was incubated with pre-equilibrated SMB in 50 mM Tris, 150 mM NaCL, 0.02% tween-20, pH 8.0 at room temperature for 50 minutes. The beads were then washed three times. Master mix (2 μl) was added into each tube, and other components were added as detailed in Table 1 below. The final volume of the reaction was 20 μl/tube in 1× reaction buffer (20 mM Tris, 100 mM NaCl, 2 mM $MgCl_2$, 0.2 mM DTT, 0.2 mg/ml BSA) and HincII. The reaction was incubated at room temperature for 35 minutes, and 10 μl of the reaction was then transferred into a 384-well plate and read at ex. 485 nm, em. 535 nm (FIG. 5).

Figure 6:
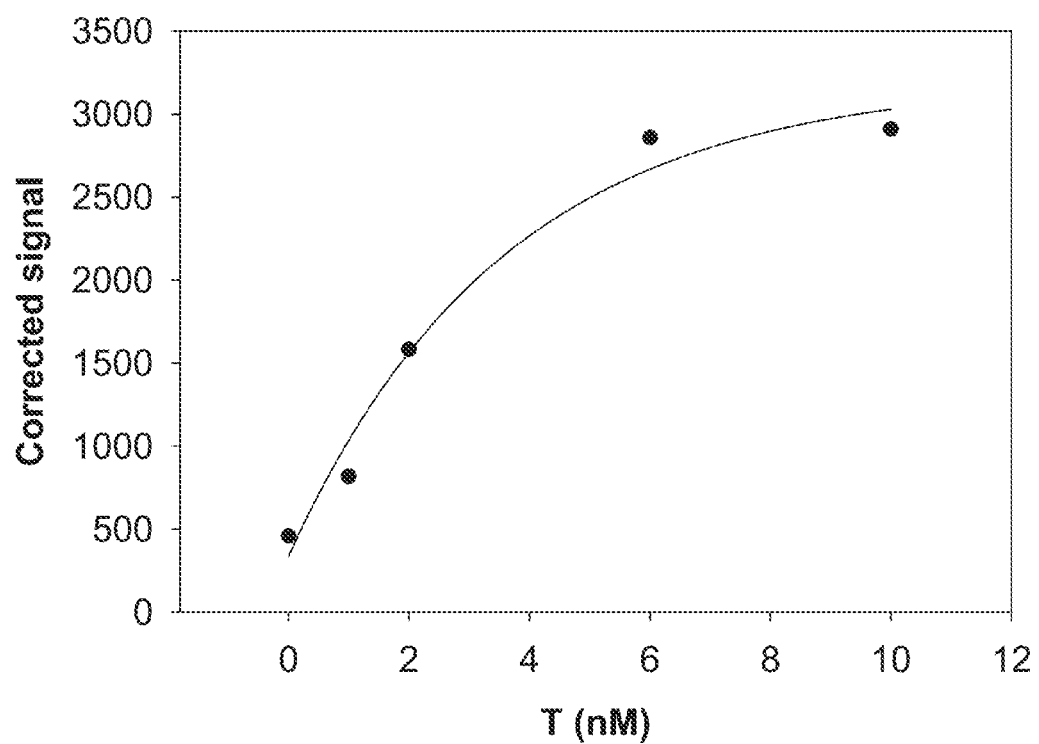
FIG. 6 depicts anti-HRP ELISA signal increase in supernatant when increasing concentrations of the target are added to a three-component molecular biosensor attached to a bead. Molecular biosensor, target and restriction enzyme were added simultaneously.

A similar experiment was performed using an oligonucleotide construct labeled with horse radish peroxidase (HRP). Master mix (2 μl) was added into each tube, and other components were added as detailed in Table 1 below. The final volume of the reaction was 35 μl/tube in 1× reaction buffer (20 mM Tris, 100 mM NaCl, 2 mM MgCl2, 0.2 mg/ml BSA) and HincII. The reaction was incubated at room temperature for 40 minutes, and 30 μl of the reaction was then transferred into a 96-well plate and mixed with 40 μl chemiluminescent ELISA substrate, and luminescence read (FIG. 6).

Example 5

Figure 7:
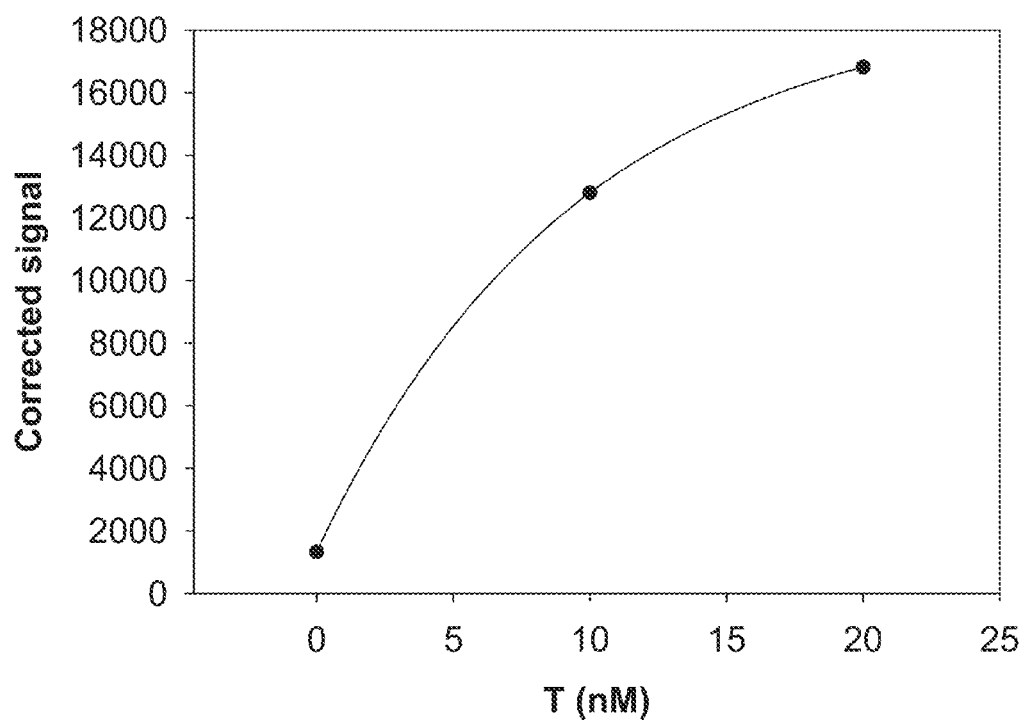
FIG. 7 depicts FAM signal increase in supernatant with increasing concentrations of the target when the restriction enzyme is added after incubation of a target with a three-component molecular biosensor attached to a bead.

Three Component Molecular Biosensor Immobilized on Magnetic Beads and Sequential Addition of Target and Restriction Enzyme In a variation of the above conditions, the FAM-labeled oligonucleotide construct immobilized on beads was mixed with the epitope binding constructs and the target molecule, and the mixture incubated at RT in binding buffer (50 mM Tris, pH 8.0, 150 mM $NaCl_2$, 0.02% Tween-20, 0.2 mg/ml BSA) for 20 min, then washed 1× with 50 μl binding buffer. This was followed by the addition of 1×HincII buffer (20 mM Tris, pH 8.0, 100 mM NaCl, 2 mM $MgCl_2$, 0.2 mM DTT, 0.2 mg/ml BSA) with HincII, for a final volume of 25 μl. The mixture was incubated at room temperature for 50 min. HincII-mediated release of FAM signal was measured using 22 μl of the reaction in a 384 well plate (FIG. 7).

Example 6

Three Component Molecular Biosensor Immobilized on Plate Surface

Figure 8:
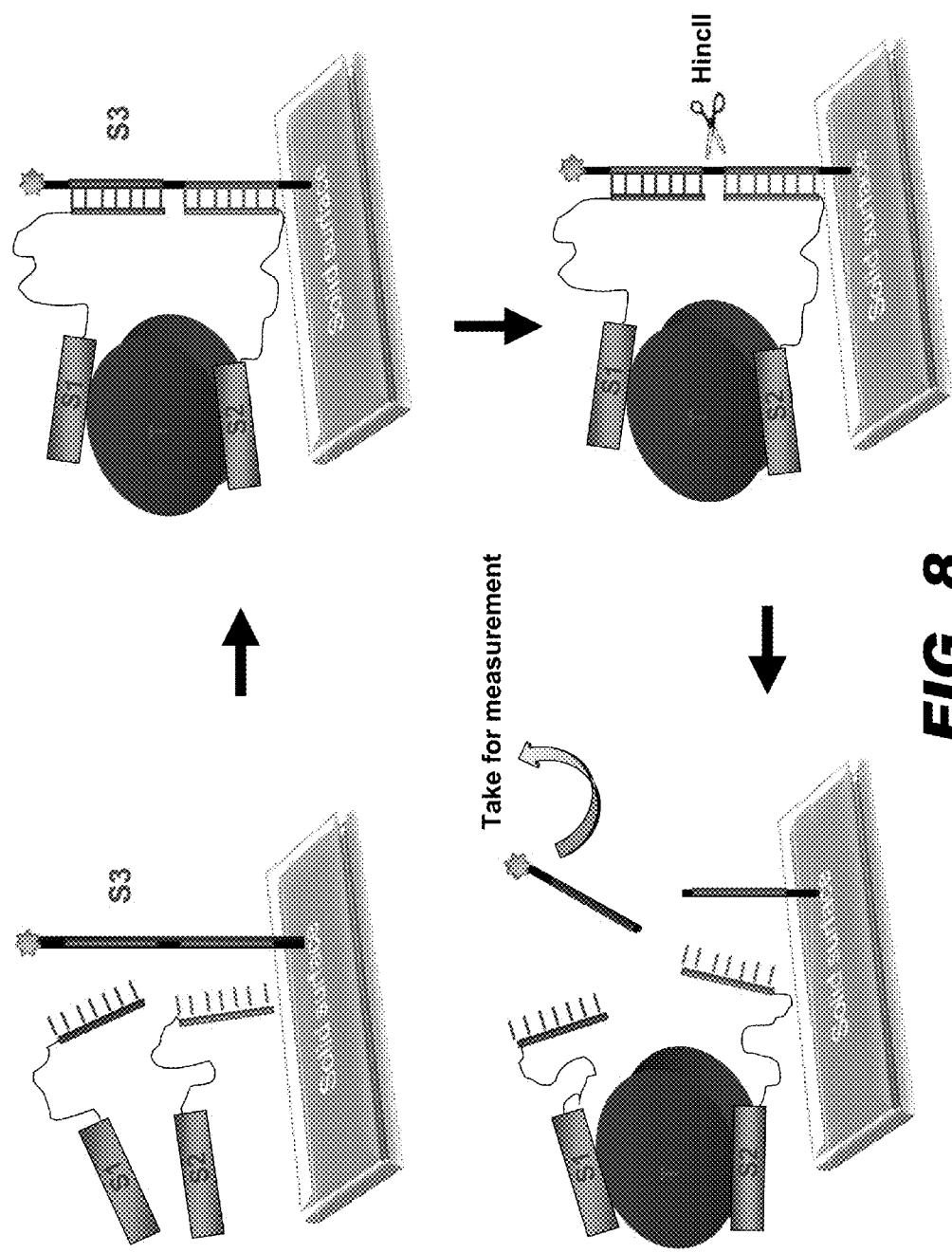
FIG. 8 depicts the overall design and function of a three-component molecular biosensor comprising a signaling oligonucleotide attached to a solid surface.
Figure 9:
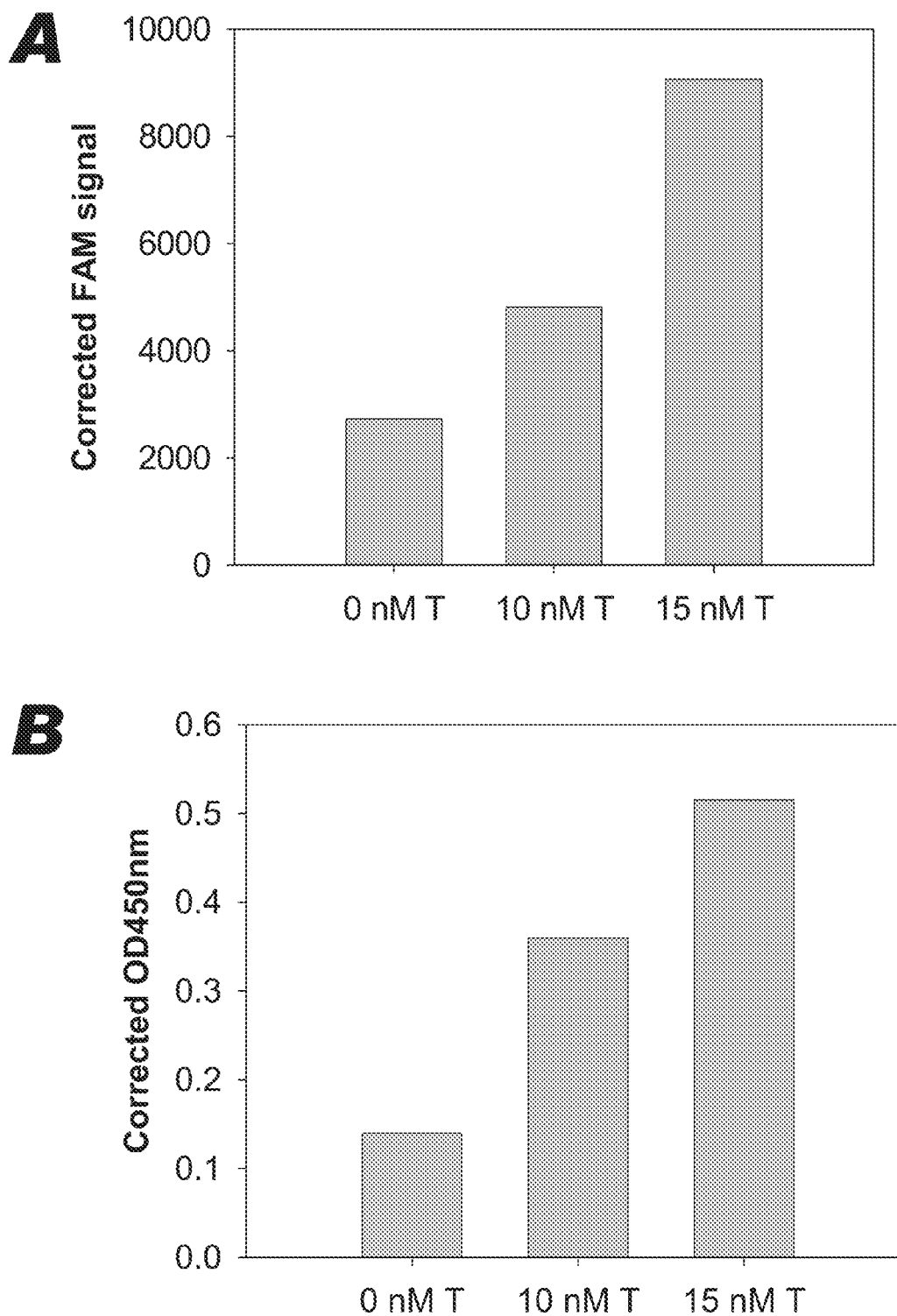
FIG. 9 depicts FAM signal increase (A) or HRP ELISA signal increase (B) in supernatant with increasing concentrations of the target using a three-component molecular biosensor attached to a solid surface.

In this Example, a FAM or HRP-labeled oligonucleotide construct described in Example 3 was immobilized on a plate (FIG. 8). The plate was coated with 30 μl of 400 nM streptavidin and incubated overnight at 4° C. The plate was then blocked with 1% BSA at room temperature for 3 hr, and washed with TBS 3 times. This was followed by the addition of 30 μl 200 nM S4, 180 nM S3, 160 nM A2-FAM, and incubated at room temperature for 2.5 hr, then washed with TBS 4 times. 25 μl of each sample was added, followed by 1×HincII buffer (20 mM Tris, pH 8.0, 100 mM NaCl, 2 mM $MgCl_2$, 0.2 mM DTT, 0.2 mg/ml BSA) and 3 units of HincII enzyme. The reaction was incubated at room temperature for 30 min. For FAM, 20 μl of the reaction was taken into a 384-well plate and read at ex. 485 nm, em. 535 nm (FIG. 9A). For HRP, 20 μl was taken into an ELISA plate, 20 μl of $TMB/H_2O_2$ mix was added and the OD450 nm was measured (FIG. 9B).

Example 7

Figure 10:
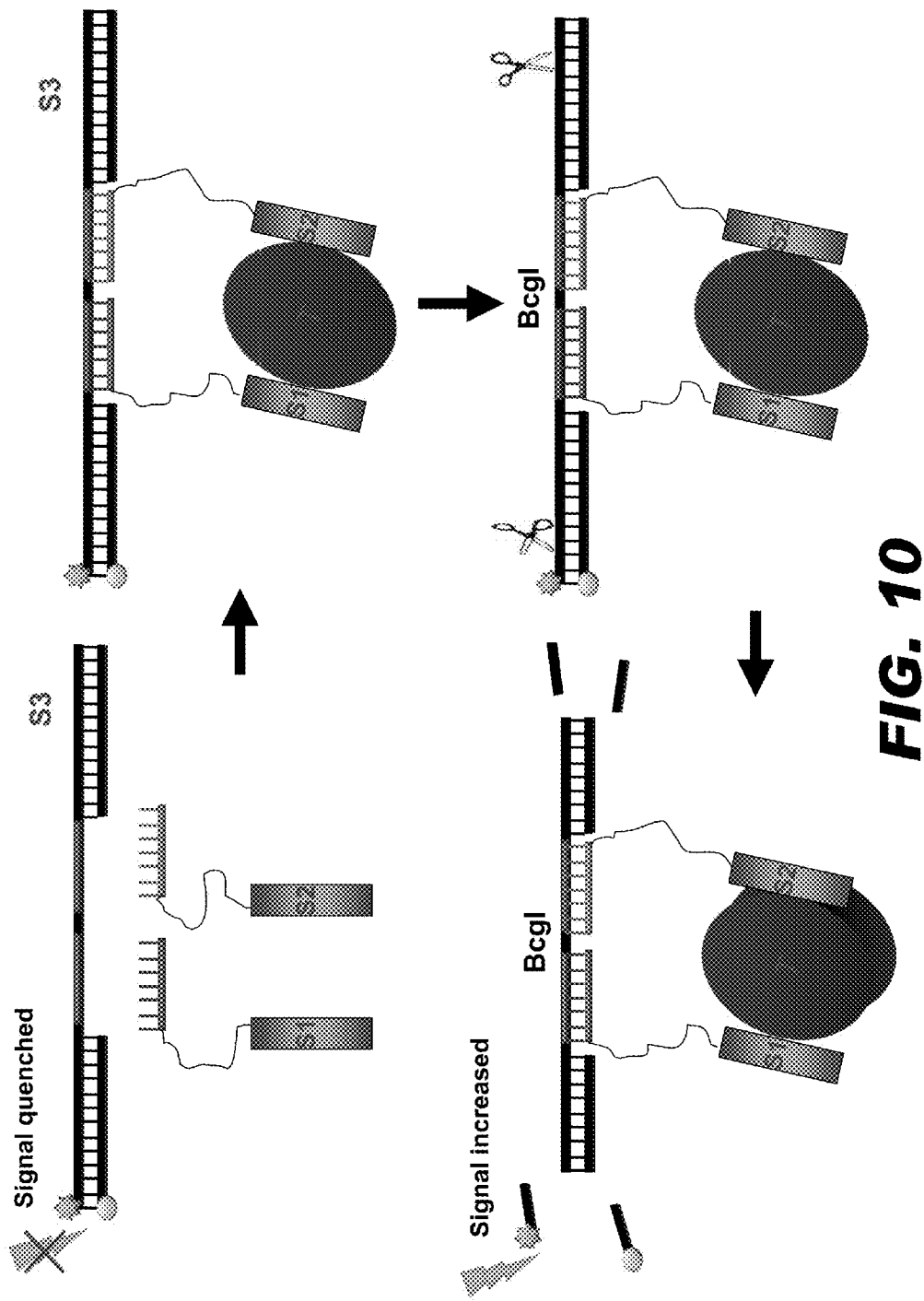
FIG. 10 depicts the overall design and function of a three-component molecular biosensor comprising a signaling oligonucleotide not attached to a solid support.

Three Component Molecular Biosensor Comprising Signaling Oligonucleotide Construct with Double-Stranded Nucleotide Regions This Example describes a method for the rapid and sensitive detection of a target molecule using a three-component molecular biosensor (FIG. 10). The three component biosensor comprises two epitope-binding agent constructs and an oligonucleotide construct comprising regions that are double-stranded and regions that are single-stranded. The oligonucleotide construct also comprises two signaling molecules, each attached to one strand of the double-stranded region of the oligonucleotide construct. Detection of a target molecule typically involves target-molecule induced co-association of the two epitope-binding agent constructs that each recognize distinct epitopes on the target molecule. The epitope-binding agent constructs each comprise non-complementary single-stranded nucleotide sequences that are complementary to two distinct, but contiguous single-stranded regions of the oligonucleotide construct, producing a double-stranded nucleic acid comprising a restriction enzyme recognition site. A type IIS restriction endonuclease enzyme releases the signaling molecule from the double stranded nucleic acid, resulting in a detectable and quantifiable change in signal intensity.

Figure 11:
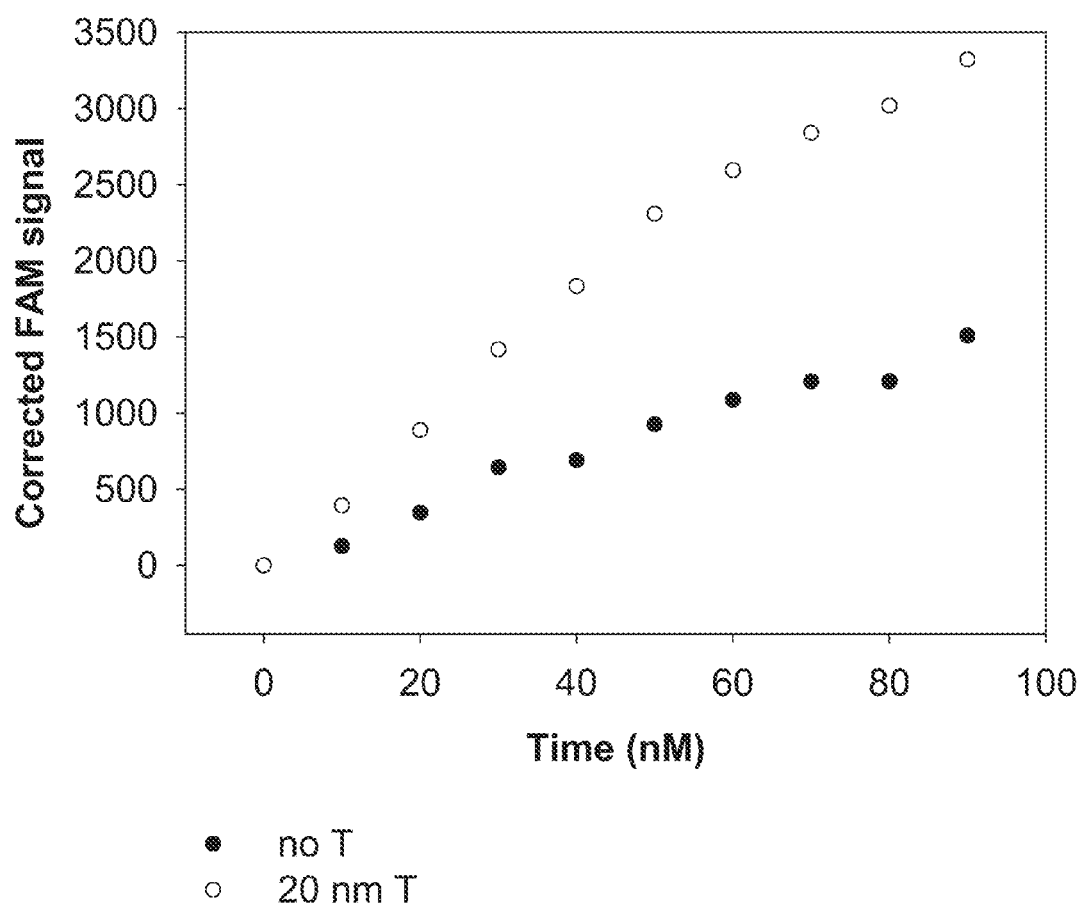
FIG. 11 depicts FAM signal increase with increasing concentrations of the target using a three-component molecular biosensor not attached to a solid support.

The oligonucleotide construct, the epitope-binding constructs, and the restriction enzyme BcgI were incubated in the presence or absence of molecular target in buffer (100 mM NaCl, 50 mM Tris, pH 7.9, 2 mM $MgCl_2$, 0.2 mM DTT, 0.2 mg/ml BSA, 20 μM SAM) in a final reaction volume of 20 μl. The reaction mixture was incubated at room temperature. Samples were taken at time 0 and every 10 minutes for measurement of FAM fluorescence (Table 1 and FIG. 11).

TABLE 1

| | |
|---|---|
| Signaling oligonucleotide construct | 60 nM |
| Epiptope oiligonucleotide constrct 1 | 20 nM |

TABLE 1-continued

| | Epiptope oiligonucleotide constrct 1 | 20 nM | |
|---|---|---|---|
| | Molecular target | 0 | 20 nM |
| | Bcgl | 2 units | 2 units |
| 0 min | | 0 | 0 |
| 10 min | | 125 | 393 |
| 20 min | | 345 | 888 |
| 30 min | | 643 | 1417 |
| 40 min | | 689 | 1833 |
| 50 min | | 925 | 2308 |
| 60 min | | 1086 | 2594 |
| 70 min | | 1208 | 2839 |
| 80 min | | 1210 | 3017 |
| 90 min | | 1508 | 3321 |
| 100 min | | 1524 | 3295 |

Example 8

Figure 12:
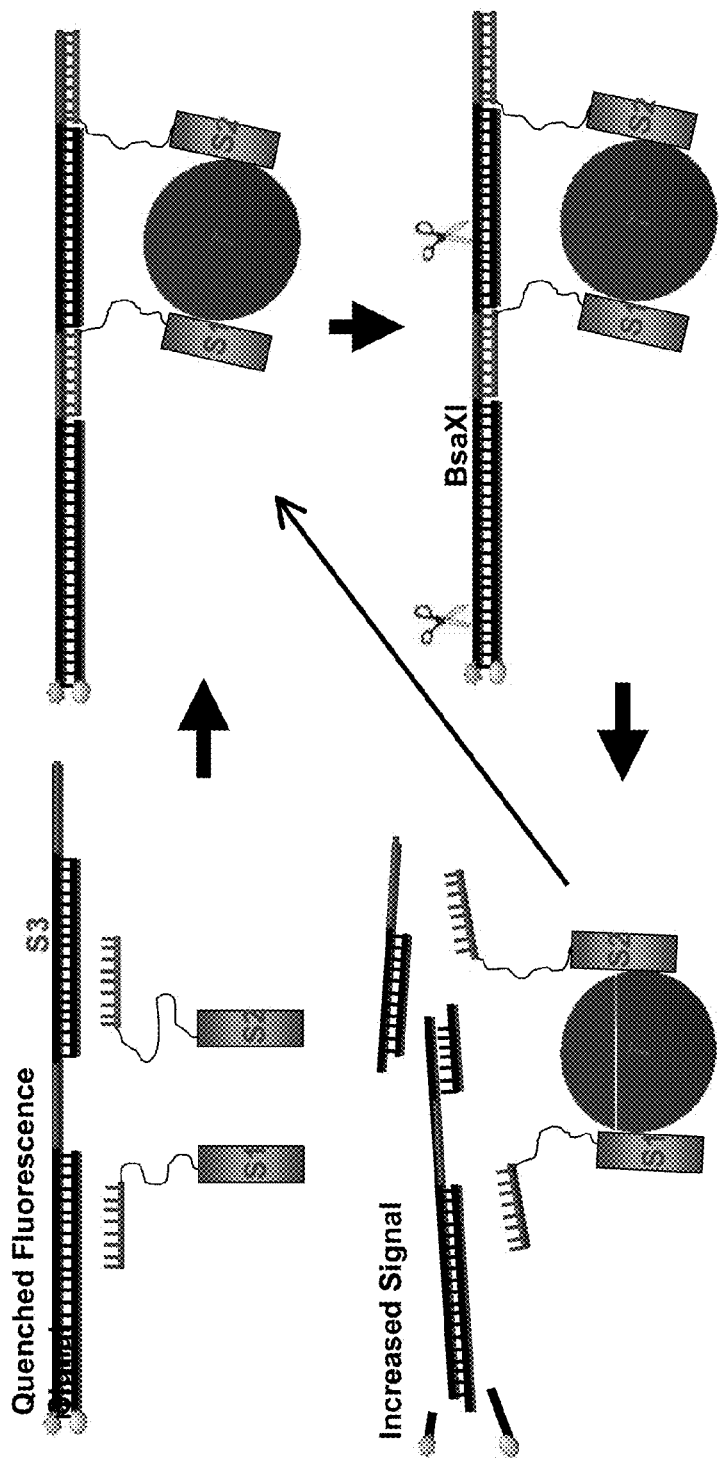
FIG. 12 depicts the overall design and function of a three-component molecular biosensor comprising a signaling oligonucleotide not attached to a solid support, using a restriction endonuclease that cleaves outside the recognition sequence.

Three Component Molecular Biosensor Comprising Signaling Oligonucleotide Construct with Double-Stranded Nucleotide Regions, with Amplified Signal This Example describes a three-component molecular biosensor wherein the three component biosensor comprises two epitope-binding agent constructs and an oligonucleotide construct comprising regions that are double-stranded and regions that are single-stranded. The oligonucleotide construct also comprises two signaling molecules, each attached to one strand of the double-stranded region of the oligonucleotide construct. The single-stranded regions of the oligonucleotide construct of this example are not contiguous, such that the signaling oligonucleotide construct comprises alternating double-stranded and single stranded regions (FIG. 12). Detection of a target molecule typically involves target-molecule induced co-association of two epitope-binding agent constructs that each recognize distinct epitopes on the target molecule. The epitope-binding agent constructs each comprise non-complementary single-stranded nucleotide sequences that are complementary to two distinct non-contiguous regions of the oligonucleotide construct. Co-association of the two epitope-binding agent constructs with the target molecule results in annealing of each signaling oligonucleotide to the oligonucleotide construct, producing a double-stranded nucleic acid comprising a restriction enzyme recognition site. A type IIS restriction endonuclease enzyme releases the signaling molecule from the double stranded nucleic acid, resulting in a detectable and quantifiable change in signal intensity. The restriction endonuclease enzyme also cleaves on the other side of the recognition sequence, within the double-stranded region of the signaling oligo construct resulting in the dissociation of the complex comprising the target and the epitope binding constructs. The complex is now free to associate with a new signaling oligonucleotide construct resulting in amplification of the signal generated from a single target.

What is claimed is:

1. A molecular biosensor consisting of a plurality of constructs, the constructs consisting of:

$R^1$—$R^2$—$R^3$;

$R^4$—$R^5$—$R^6$; and at least one $R^7$—$R^8$—$R^9$;

wherein:
$R^1$ is an antibody or antibody fragment that binds to a first epitope on a polypeptide or protein;
$R^2$ is a flexible linker attaching $R^1$ to $R^3$;
$R^3$ and $R^6$ are a first pair of nucleotide sequences that are complementary to two distinct regions on $R^8$;
$R^5$ is a flexible linker attaching $R^4$ to $R^6$;
$R^4$ is an antibody or antibody fragment that binds to a second epitope on the polypeptide or protein;
$R^8$ is an oligonucleotide construct comprising a first region that is complementary to $R^3$ and a second region that is complementary to $R^6$, such that in the absence of the polypeptide or protein, $R^7$ and $R^8$ do not produce detectable signal, and in the presence of the polypeptide or protein, $R^3$ and $R^6$ associate with $R^8$, creating a restriction endonuclease site that is cleaved by a restriction endonuclease that recognizes the restriction endonuclease site, wherein upon cleavage of the restriction endonuclease site, $R^7$ dissociates, producing detectable signal;
$R^7$ is a signaling molecule; and
$R^9$ is a solid support.

2. The molecular biosensor of claim 1, wherein a free energy for association of $R^3$ and $R^8$, and $R^6$ and $R^8$ are from about −5.5 kcal/mole to about −8.0 kcal/mole at a temperature from about 21° C. to about 40° C., and a salt concentration from about 1 mM to about 100 mM.

3. The molecular biosensor of claim 1, wherein $R^3$ and $R^6$ are independently from about 2 to about 20 nucleotides in length.

4. The molecular biosensor of claim 1, further comprising a plurality of $R^7$—$R^8$—$R^9$.

5. A method for determining the presence of a polypeptide or protein in a sample, the method comprising:
a) combining a molecular biosensor of claim 1 with the polypeptide or protein;
b) adding a restriction endonuclease that recognizes the double-stranded restriction endonuclease recognition site formed by $R^3$, $R^6$ and $R^8$;
c) measuring the release of the $R^7$ signaling molecule from the $R^9$ solid support, wherein an increase in signal indicates the presence of a target molecule.

6. A molecular biosensor consisting of a restriction enzyme and a plurality of constructs, the constructs consisting of:

$R^1$—$R^2$—$R^3$;

$R^4$—$R^5$—$R^6$; and at least one $R^7$—$R^8$;

wherein:
$R^1$ is an antibody or antibody fragment that binds to a first epitope on a polypeptide or protein;
$R^2$ is a flexible linker attaching $R^1$ to $R^3$;
$R^3$ and $R^6$ are a first pair of nucleotide sequences that are complementary to two distinct regions on $R^8$;
$R^5$ is a flexible linker attaching $R^4$ to $R^6$;
$R^4$ is an antibody or antibody fragment that binds to a second epitope on the polypeptide or protein;
$R^8$ is an oligonucleotide construct comprising a first region that is complementary to $R^3$ and a second region that is complementary to $R^6$, such that in the absence of the polypeptide or protein, $R^7$ and $R^8$ do not produce detectable signal, and in the presence of the polypeptide or protein, $R^3$ and $R^6$ associate with $R^8$, creating a restriction endonuclease site that is cleaved by a restriction endonuclease that recognizes the restriction endonuclease site, wherein upon cleavage of the restriction endonuclease site, $R^7$ dissociates, producing detectable signal; and $R^7$ is a signaling molecule.

7. The molecular biosensor of claim 6, wherein a free energy for association of $R^3$ and $R^8$, and $R^6$ and $R^8$ are from about −5.5 kcal/mole to about −8.0 kcal/mole at a temperature from about 21° C. to about 40° C., and a salt concentration from about 1 mM to about 100 mM.

8. The molecular biosensor of claim 6, wherein $R^3$ and $R^6$ are independently from about 2 to about 20 nucleotides in length.

9. The molecular biosensor of claim 6, further comprising a plurality of $R^7$—$R^8$.

10. A method for determining the presence of a polypeptide or protein in a sample, the method comprising:
    a) combining a molecular biosensor of claim 6 with the polypeptide or protein;
    b) contacting the molecular biosensor with a restriction endonuclease that recognizes the double-stranded restriction endonuclease recognition site formed by $R^3$, $R^6$ and $R^8$;
    c) measuring the release of the $R^7$ signaling molecule from $R^8$.

* * * * *